(12) United States Patent  
Berdel et al.

(10) Patent No.: US 8,362,205 B2  
(45) Date of Patent: Jan. 29, 2013

(54) DELOCALIZATION MOLECULES AND USE THEREOF

(75) Inventors: Wolfgang Berdel, Münster (DE); Carsten Müller-Tidow, Münster (DE); Hubert Serve, Münster (DE); Björn Steffen, Münster (DE)

(73) Assignees: Carsten Müller-Tidow, Münster (DE); Wolfgang Berdel, Münster (DE); Hubert Serve, Münster (DE); Björn Steffen, Franfurt am Main (DE); Oncoscience AG, Wedel (DE); Ari E. Bisimis, Königsstein (DE)

( * ) Notice: Subject to any disclaimer, the term of this patent is extended or adjusted under 35 U.S.C. 154(b) by 1170 days.

(21) Appl. No.: 10/531,415

(22) PCT Filed: Oct. 17, 2003

(86) PCT No.: PCT/EP03/11525  
§ 371 (c)(1),  
(2), (4) Date: Nov. 22, 2005

(87) PCT Pub. No.: WO2004/037278  
PCT Pub. Date: May 6, 2004

(65) Prior Publication Data  
US 2006/0166876 A1 Jul. 27, 2006

(30) Foreign Application Priority Data  
Oct. 18, 2002 (DE) .................................. 102 48 751

(51) Int. Cl.  
*C07K 14/00* (2006.01)  
*C07K 4/00* (2006.01)  
*A61K 38/00* (2006.01)  
*A61P 35/00* (2006.01)  
*A61P 43/00* (2006.01)

(52) U.S. Cl. ........ 530/350; 530/300; 514/1.1; 514/18.9; 514/19.2; 514/19.3

(58) Field of Classification Search ........................ None  
See application file for complete search history.

(56) References Cited

U.S. PATENT DOCUMENTS

2003/0105000 A1* 6/2003 Pero et al. ........................ 514/12  
2006/0019256 A1* 1/2006 Clarke et al. ...................... 435/6

FOREIGN PATENT DOCUMENTS

WO WO 01/73433 A2 * 10/2001  
WO WO 02/00024 A1 * 1/2002

OTHER PUBLICATIONS

Gura (Science, 1997, 278:1041-1042).*  
Kaiser (Science, 2006, 313: 1370).*  
Freshney (Culture of Animal Cells, A Manual of Basic Technique, Alan R. Liss, Inc., 1983, New York, p. 3-4).*  
Dermer (Bio/Technology, 1994, 12:320).*  
Zips et al. (In vivo, 2005, 19:1-7).*  
Lloyd et al. (Int. J. Cancer 1997 71:842-850).*  
McWhirter et al. (Mol. and Cell. Biol. 1993, 13: 7587-759).*  
Muller et al. (Mol. and Cell. Biol. 1992, 12:5087-5093).*  
Prokocimer et al. (Blood 1994 84:2391-2411).*  
Nussey and Whitehead (Endocrinology: An Integrated Approach Box 3.9, 2001).*  
Wu et al. (Oncogene 1999, 18: 4416-4424).*  
Melnick et al. (Blood Dec. 2000, 96: 3939-3947).*  
Mao et al. (Blood Dec. 2000, 96: 3939-3947).*  
DiMartino and Cleary (Br. J. Haematology 1999, 106: 614-626).*  
Bowie et al (Science, 1990, 247:1306-1310).*  
Skolnick et al. (TIBTECH 18:34-39, 2000).*  
Ibragimova and Eade (Biophysical Journal, Oct. 1999, vol. 77, pp. 2191-2198).*  
Scott et al. (Nature Genetics, 1999, 21:440-443).*  
Coutinho et al. (Blood 2000: 96: 618-624).*  
Muller et al. (Mol. & Cell. Biol. 1992 12:5087-5093).*  
Alberts et al. (Mol. Biol. of the Cell. 4th ed. The Transport of Molecules between the Nucleus and the Cytosol, New York, Garland Science, 2002).*  
Aryee et al. (Cancer Res. Oct. 15, 2006 66(20): 9862-9869).*  
Üren & Toretsky (Future Oncol. 2005 1(4): 521-528).*  
Bischoff, et al., "An Adenovirus Mutant That Replicates Selectively in p53-Deficient Human Tumor Cells", *Science*, vol. 274, pp. 373-376 (1996).  
Britos-Bray and Friedman, "Core Binding Factor Cannot Synergistically Activate the Myeloperoxidase Proximal Enhancer in Immature Myeloid Cells without c-Myb", *Molecular and Cellular Biology*, vol. 17, No. 9, pp. 5127-5135 (1997).  
Daley, et al., "Induction of Chronic Myelogenous Leukemia in Mice by the P210bcr/abl Gene of the Philadelphia Chromosome", *Science*, vol. 247, pp. 824-830 (1990).  
Darzynkiewicz, et al., "Flow Cytometry in Analysis of Cell Cycle and Apoptosis", *Seminars in Hematology*, vol.38, No. 2, pp. 179-193 (2001).  
Downing, "The AML1-ETO Chimaeric Transcription Factor in Acute Myeloid Leukaemia: Biology and Clinical Significance", *British Journal of Haematology*, vol. 106, pp. 296-308 (1999).  
Frank, et al., "The AML1/ETO fusion protein blocks transactivation of the GM-CSF promoter by AML1B", *Oncogene*, vol. 11, pp. 2667-2674 (1995).  
Gewirtz and Calabretta, "A c-*myb* Antisense Oligodeoxynucleotide Inhibits Normal Human Hematopoiesis in Vitro", *Science*, vol. 242, pp. 1303-1306 (1988).  
Gewirtz, "Myb targeted therapeutics for the treatment of human malignancies", *Oncogene*, vol. 18, pp. 3056-3062 (1999).  
Lenny, et al., "Functional domains of the t(8;21) fusion protein, AML-1/ETO", *Oncogene*, vol. 11, 1761-1769 (1995).  
Linggi, et al., "The t(8;21) fusion protein, AML1-ETO, specifically represses the transcription of the $p14^{ARF}$ tumor suppressor in acute myeloid leukemia", *Nature Medicine*, vol. 8, No. 7, pp. 743-750 (2002).  
Mao, et al., "Functional and Physical Interactions between AML1 Proteins and an ETS Protein, MEF: Implications for the Pathogenesis of t(8;21)-Positive Leukemias", *Molecular and Cellular Biology*, vol. 19, No. 5, pp. 3635-3644 (1999).

(Continued)

*Primary Examiner* — Peter J Reddig  
(74) *Attorney, Agent, or Firm* — Arnold & Porter LLP

(57) ABSTRACT

The invention relates to delocalization molecules, methods for the production thereof, and the use thereof as medicaments, especially for treating tumors.

19 Claims, 13 Drawing Sheets

OTHER PUBLICATIONS

McCormick, "Interactions between adenovirus proteins and the p53 pathway: the development of ONYX-015)", *Seminars in Cancer Biology*, vol. 10, pp. 453-459 (2000).

Meyers, et al., "The t(8;21) Fusion Protein Interferes with AML-1B-Dependent Transcriptional Activation", *Molecular and Cellular Biology*, vol. 15, No. 4, pp. 1974-1982 (1995).

Mizuki, et al., "Flt3 mutations from patients with acute myeloid leukemia induce transformation of 32D cells mediated by the Ras and STAT5 pathways", *Blood*, vol. 96, No. 12, pp. 3907-3914 (2000).

Mucenski, et al., "A Functional c-myb Gene Is Required for Normal Murine Fetal Hepatic Hematopoiesis", *Cell*, vol. 65, pp. 677-689 (1991).

Müller, et al., "c-myb Transactivates the Human Cyclin A1 Promoter and Induces Cyclin A1 Gene Expression", *Blood*, vol. 94, No. 12, pp. 4255-4262 (1999).

Müller, et al., "Methylation of the Cyclin A1 Promoter Correlates with Gene Silencing in Somatic Cell Lines, while Tissue-Specific Expression of Cyclin A1 is Methylation Independent", *Molecular and Cellular Biology*, vol. 20, No. 9, pp. 3316-3329 (2000).

Müller-Tidow, et al., "Redirection of Oncoproteins to Kill Cancer Cells", *Cell Cycle*, vol. 2, No. 6, pp. 531-533 (2003).

Oelgeschlager, et al., "C/EBP, c-Myb, and PU.1 Cooperate to Regulate the Neutrophil Elastase Promotor", *Molecular and Cellular Biology*, vol. 16, No. 9, pp. 4717-4725 (1996).

Pabst, et al., "AML1-ETO downregulates the granulocytic differentiation factor C/EBPα in t(8;21) myeloid leukemia", *Nature Medicine*, vol. 7, No. 4, pp. 444-451 (2001).

Ratajczak, et al., "In vivo treatment of human leukemia in a *scid* mouse model with c-myb antisense oligodeoxynucleotides", *Proc. Natl. Acad. Sci. USA*, vol. 89, pp. 11823-11827 (1992).

Sakura, et al., "Delineation of three functional domains of the transcriptional activator encoded by the c-*myb*protooncogene", *Proc. Natl. Acad. Sci. USA*, vol. 86, pp. 5758-5762 (1989).

Steffen, et al., "Specific protein redirection as a transcriptional therapy approach for t(8;21) leukemia", *PNAS*, vol. 100, No. 14, pp. 8448-8453 (2003).

Stein, et al., "Subnuclear Organization and Trafficking of Regulatory Proteins: Implications for Biological Control and Cancer", *Journal of Cellular Biochemistry*, Supplement 35, pp. 84-92 (2000).

Taylor, et al., "A dominant interfering Myb mutant causes apoptosis in T cells", *Genes and Development*, vol. 10, pp. 2732-2744 (1996).

Vigneri and Wang, "Induction of apoptosis in chronic myelogenous leukemia cells through nuclear entrapment of BCR-ABL tyrosine kinase", *Nature Medicine*, vol. 7, No. 2, pp. 228-234 (2001).

Wang, et al., "ETO, fusion partner in t(8;21) acute myeloid leukemia, represses transcription by interaction with the human N-CoR/mSin3/HDAC1 complex", *Proc. Natl. Acad. Sci. USA*, vol. 95, pp. 10860-10865 (1998).

White and Weston, "Myb is required for self-renewal in a model system of early hematopoiesis", *Oncogene*, vol. 19, pp. 1196-1205 (2000).

Ziebold, et al., "Phosphorylation and activation of B-Myb by cyclin A-Cdk2", *Current Biology*, vol. 7, No. 4, pp. 253-260 (1997).

Petermann, R., et al., "Oncogenic EWS-Fli1 interacts with hsRPB7, a subunit of human RNA polymerase II," Oncogene 17, pp. 603-610 (1998).

Chansky, H., et al., "Oncogenic TLS/ERG and EWS/Fli-1 Fusion Proteins Inhibit RNA Splicing Mediated by YB-1 Protein," Cancer Research 61, pp. 3586-3590 (2001).

Watson, D., et al., FLI1 and EWS-FLI1 function as ternary complex factors and ELK1 and SAP1a function as ternary and quaternary complex factors on the Egr1 promoter serum response elements, Onocogene14, pp. 213-221 (1997).

Erkizan, H., et al., "Oncogenic Partnerships: EWS-FLI1 Protein Interactions Initiate Key Pathways of Ewing's Sarcoma," Clinical Cancer Research, 16:4077-4083 (2010).

Knoop, L., et al., "The Splicing Factor U1C Represses EWS/FLI-mediated Transactivation," J. Bio. Chem., 275:32, pp. 24865-24871 (2000).

Knoop, L., et al., "EWS/FLI Alters 5'-Splice Site Selection," J. Bio. Chem., 276:25, pp. 22317-22322 (2001).

Yang, L., et al., "EWS FL1-1 Fusion Protein Interacts with Hyperphosphorylated RNA Polymerase II and Interferes with Serine-Arginine Protein-mediated RNA Splicing," J. Bio. Chem., 275:48, pp. 37612-37618 (2000).

\* cited by examiner

DELOCALIZATION MOLECULES AND USE THEREOF

CROSS-REFERENCE TO RELATED APPLICATIONS

This application is a national phase application under 35 U.S.C. §371 of International Application No. PCT/EP03/011525, filed Oct. 17, 2003, the disclosure of which is hereby incorporated by reference in its entirety, and claims the benefit of German Patent Application No. 102 48 751.0, filed Oct. 18, 2002.

INCORPORATION OF SEQUENCE LISTING

A paper copy of the Sequence Listing is herein incorporated by reference in its entirety.

The present invention relates to dyslocalization molecules, methods for their preparation and their use as medicaments, in particular for the treatment of tumors.

The localization of a protein, that is to say the location site in a cell, in a tissue or in the plasma has a substantial influence on the function and activity of the protein. This particularly applies to proteins involved in cell regulation.

Eukaryotic cells comprise intracellular membranes which divide almost one half of the cell contents into spatially separate compartments referred to as, organelles. The main types of membrane-enclosed organelles occurring in all eukaryotic cells are the endoplasmic reticulum, the Golgi apparatus, the cell nucleus, the mitochondria, the lysosomes; the endosomes and the peroxisomes. Each organelle has a particular set of proteins which ensures maintenance of the organelle-specific functions.

Newly synthesized proteins make their way from the cytosol, where they are formed, to the organelle, in which they carry out specific tasks, by following a specific transport pathway. The transport pathway is defined by signals in the form of signal peptides or signal regions in the amino acid sequence of the protein. These signal peptides are recognized by corresponding receptors of the target organelle. Proteins which carry out their task in the cytosol comprise no signal peptides and therefore remain in the cytosol (Alberts et al., Molekularbiologie der Zelle; VCH Verlag, 3rd edition).

Furthermore, the targeted localization of proteins is achieved by their organization as multimeric complexes which can be specifically transported to subcellular structures. These complexes are held at appropriate sites through their affinity for anchor or scaffold proteins and by means of other structural components at this site. The affinity of individual proteins for these structures depends on the appropriate localization domains, post-translational modifications, alosteric changes and other effects (Stein et al;, J. Cell. Biochem., Suppl. (2000), pp. 84-92).

The function of various protein families having DNA-binding and transactivating activity, such as, for example, Catenin, Notch or STAT proteins, depends essentially on transport from the cytosol into the cell nucleus.

In many disorders, functional consequences of a mutation result in altered localization of the mutated gene products. In chronic myeloid leukemia (CML) for example, the transforming potential of Bcr-Abl depends not only on the activated kinase activity of Abl but also on the impaired, actin-bound localization of the protein. Due to this localization, both mitogenic and anti-apoptotic signal pathways are activated, resulting in the transforming activity (Daley et al., Science, Vol. 247 (1990), pp. 824-830).

Nuclear inclusion of Bcr-Abl by nonspecific inhibition of the nuclear export machinery leads for example to apoptosis of Bcr-Abl positive cells (Vigneri P. & Wang J. W., Nat. med., Vol. 7 (2001), pp. 228-234).

In acute myeloid leukemia (AML), the malignant transformation is often associated with protein dyslocalization. The most frequent chromosomal translocations generate chimeric proteins which comprise transcription factors, frequently leading to fusion of the DNA-binding domain of a transcription activator to a transcription repressor. Thus, the transcription repressor is transported wrongly to the target genes of the transcription activator.

The most frequent chromosomal translocation in AML is the t(8;21) translocation which is found in 10-15% of adult patients afflicted with this disease (Downing J. R., Br. J. Haematol. Vol. 106 (1999), pp. 296-308). Because of this translocation, the C-terminal end of the transcription activator AML1 is replaced by the transcription repressor ETO and generates the AML1-ETO fusion protein (Meyers et al., Mol. Cell. Biol., Vol. 15. (1995), pp. 1974-1982;and Lenny et al.;, Oncogene, Vol. 11 (1995), 1761-1769).

The AML1-ETO fusion protein is able to effect binding of various corepressors and histone deacetylases (HDACs), and in this way to inhibit expression of the AML1 target genes, for example of GM-CSF, of neutrophil elastase and c/EBPα (Britos-Bray, M. & Friedman, A. D., Mol. Cell. Biol., Vol. 17 (1997), pp. 5127-5135); Frank et al., Oncogene, Vol. 11 (1995), pp. 2667-2674); Pabst, et al., Nat. Med.,Vol. 7 (2001), pp. 444-451;and Oelgeschlager et al., Mol. Cell. Biol., Vol. 16 (1996), pp. 4717-25). It can be assumed that this effect of AML1-ETO is responsible for the AML-typical blockade of differentiation.

Neoplastic diseases are at present normally treated by a combination of surgical procedure, irradiation and administration of chemotherapeutic agents. The therapy of hematological neoplastic diseases is restricted in particular to the administration of chemotherapeutic agents. However, conventional chemotherapeutic approaches, as well as irradiation, do not act specifically on the cancer cells. Therefore, the therapy is always associated with serious side effects for the patient because the effect of the particular therapeutic approach affects all proliferating cells.

The side effects of chemotherapy may lead to acute renal failure and organic damage caused by toxicity to the heart, lung, liver and nervous system. The consequence which must be expected from the immunosuppressant effect of this therapy is an increased number of infections leading to fatality. Many therapies are unsuitable because of their toxicity in particular for elderly patients.

The limited availability of active agents which are directed specifically against cancer cells and attack them is a substantial reason for the prognosis with many cancer types still being very poor.

Attempts have therefore been made in the prior art to develop tumor cell-specific therapeutic approaches. Thus, a deficient adenovirus able to replicate exclusively in tumors with mutations in the p53 signal transduction pathway has been constructed (Bischoff et. al., 1996, Science, Vol. 274, pp. 373-6). By this procedure, tumor cells which have a p53 mutation are infected, whereas other cells are unaffected. The practical value of this therapy is currently being investigated in clinical trials (McCormick F., 2000, Semin. Cancer Biol., Vol. 10, pp. 453-9).

However, most therapeutic approaches are directed at the identification of small molecules which might be used as inhibitors of oncogenic proteins, for example specific inhibitors of tyrosine kinases. STI571, an inhibitor of various tyrosine kinases including Bcr-Abl, has proved to be effective against t(9;22) leukemias (Vigneri et al., 2001, Nat. Med., Vol. 7, pp. 228-34). Despite the activity of STI571 in inhibiting the molecular targets in BCR-ABL-associated disorders, full activity is achieved only in CML patients with an early (chronic phase) but not fully developed disorder. In contrast thereto, relapse is to be observed in most patients with Bcr-Abl positive acute lymphoblastic leukemia and CML blast crisis. The reason is probably that cancer is the result of a series of genetic changes, and reversal of one of these oncogenic events by an active agent is insufficient to cure the disorder.

Although molecular targets for cancer therapy are being identified at an increasing rate, scarcely any ideas have yet been developed as to how this knowledge could be utilized for specific therapies.

The present invention was thus based on the object of providing compounds which, as an active agent of a medicament, allow for the improved treatment of tumors, in particular of leukemias.

This object has now been achieved by compounds which have binding affinity for a tumor-specific molecule and are able to effect dyslocalization of said tumor-specific molecule.

For all embodiments of the present application, it is preferred that the dyslocalization of the tumor-specific molecule which is effected by the compounds of the invention inhibits the growth of tumor-specific cells or even induces apoptosis in tumor-specific cells.

In contrast to prior art therapeutic approaches, the therapeutic approach of the present invention is thus directed at dyslocalization of an oncogenic molecule, in which the function of the oncogene is not inhibited but utilized for eliminating the oncogene-containing cells. The compounds of the invention are highly specific and have no effect whatsoever on cells which do not have the tumor-specific molecule. This novel therapeutic approach therefore does not reverse individual oncogenic events, but changes a specific property of the tumor cells in such a way that the tumor cell is eliminated. In this connection, this method makes use of the fact that the function of many proteins—also of oncogenic proteins—depends not only on their shape but also quite decisively on their localization within the cell.

In one embodiment of the present invention, the compound is a peptide, oligopeptide, protein or fusion protein. However, it is likewise possible to employ small molecules which are characterized by their specific binding to the tumor-specific molecule. A large number of organic molecules can be employed in this connection. Organic molecules mean in the present connection hydrocarbons of low molecular weight. These may have a molecular weight of <5000 Da, preferably <1000 Da and particularly preferably <500 Da. It is likewise conceivable to use composite molecules consisting of two different components.

The tumor-specific molecule is a molecule which in this form is present either exclusively in tumor cells or is present in tumor cells in a different concentration than in healthy cells. The tumor-specific molecule is preferably also a peptide, oligopeptide, protein, fusion protein, RNA or DNA. Tumor-specific post-translational modifications such as phosphorylation, glycosylation, acetylation, methylation and similar modifications are also possible in this connection as tumor-specific parameters.

In one embodiment of the present invention, the tumor-specific molecule is a fusion protein which is present exclusively in tumor cells, for example the AML1-ETO molecule. Tumor-specific molecules which can be further attacked are the fusion proteins resulting from other chromosomal translocations in leukemias (Bcr-Abl, PML-RARalpha, PLZF-RARalpha, MLL fusion proteins, etc.) and in other malignant disorders (e.g. EWS-Fli in sarcomas).

The compounds of the invention show a binding affinity for tumor-specific molecules. The binding affinity is preferably in the range of $10^{-5}$ to $10^{-12}$, and particularly preferably in the range of $10^{-7}$ to $10^{-9}$.

The compounds of the invention are able to effect a dyslocalization of the tumor-specific molecules. For the purposes of the present invention, dyslocalization of a tumor-specific molecule means transport of the molecule within the cell or the tissue to a site where this molecule is not normally present in tumor cells. For example, a dyslocalization may effect a binding of tumor-specific proteins (for example transcription activators or repressors) to the genomic DNA at positions at which the tumor-specific proteins would not otherwise bind.

According to another example, dyslocalization of a tumor-specific molecule may have the result that the latter is secreted or transported into a cell organelle although it is a cytoplasmic molecule in the tumor cell. For example, the tumor-specific molecule may be exported from the nucleus although it is a nuclear molecule in tumor cells.

According to a particularly preferred embodiment of the present invention, the dyslocation of the tumor-specific molecule leads to a more than 60% inhibition of the growth of tumor cells, wherein more; than 80% inhibition is particularly preferred. The growth inhibition can be determined via a reduction in the colony formation in methylcellulose according to the method of Mizuki, M. et al. "Flt3 mutations from patients with acute myeloid leukemia induce transformation of 32D cells mediated by the. Ras and STAT5 pathways", Blood, 2000 Dec. 1, Vol. 96(12), 3907-14.

According to an alternative embodiment the dyslocalization leads to an induction of apoptosis in the tumor cells. The apoptosis in the tumor cells is increased in cells treated with the molecule of the invention as compared to untreated cells preferably by a factor of 2, wherein an increase in apoptosis by a factor of at least 3 is particularly, preferred. The increased induction of apoptosis in the tumor cells can be measured by means of standard assays (Darzynkiewitz, Z. et al., "Flow cytometry in analysis of cell cycle and apoptosis", Semin Hematol. 2001 April, Vol. 38(2)., 179-93).

According to the present invention, the dyslocalization of the tumor-specific molecule may lead for example to binding of the tumor-specific molecule to a nucleic acid sequence which regulates the transcription of a gene. The transcription of the gene may be activated or inhibited through the binding of the tumor-specific molecule.

According to a particularly preferred embodiment, the compound comprises the peptide sequence of the c-myb DNA binding domain and/or the peptide sequence of the AML1 binding domain of the MEF ("myeloid elf like factor"). According to a particularly preferred embodiment, the compound of the invention has the amino acid sequence shown in SEQ ID NO:1.

The present invention further relates to nucleic acids which encode a peptide or protein according to the invention which has binding affinity for a tumor-specific molecule and can effect dyslocalization of the tumor-specific molecule. The nucleic acid is preferably DNA or RNA. The nucleic acid may be part of a vector which may be designed for expression of the nucleic acid. According to a particularly preferred embodiment, the compound of the invention is encoded by the nucleotide sequence shown in SEQ ID NO:2.

According to a further embodiment, the present invention relates to host cells which have one of the nucleic acids of the invention.

The invention further comprises medicaments which comprise a compound, nucleic acid or host cells according to the invention. The medicament may additionally comprise a pharmaceutically acceptable carrier and be formulated for oral, intravenous or intramuscular administration.

The present invention further relates to the use of the compound, nucleic acids or host cells according to the invention for the preparation of a medicament for the treatment of tumors, leukemias, especially acute myeloid leukemia. The treatment of an acute myeloid leukemia caused by a t(8;21) translocation is particularly preferred.

Methods for preparing the compounds of the invention are further included within the scope of the present invention. In the case of a peptide or protein, the latter can be expressed recombinantly or obtained by protein synthesis.

Finally, the present invention relates to methods for identifying a compound suitable for the treatment of tumors, in which:
(a) a tumor-specific molecule is identified; and
(b) a compound which has a binding affinity for said tumor-specific molecule and is able to effect a dyslocalization of said tumor-specific molecule is identified.

Tumor-specific molecules are identified in this method by means of modern genomic and proteomic methods. It is possible to employ in this connection for example microarray analyses or 2D protein gel electrophoreses with subsequent identification by mass spectrometry and a combination of these methods.

All methods known in the art for analyzing differences between tumor cells and non-degenerated cells can be used in accordance with the invention for the identification of tumor-specific molecules.

In a second step, the target molecule which can be used for dyslocation of the tumor-specific molecule is identified. This molecule may once again be a protein, an RNA or a DNA fragment.

The screening method is preferably applied as a high-throughput method in such a way that thousands of substances are tested for their binding to the tumor-specific molecule and to the dyslocalization molecule by means of automated robotic pipettors. Subsequently, compounds which bind with high affinity and specificity to one of the two molecules or to both molecules at the same time are selected. If two different molecules are identified (with one binding to the tumor-specific molecule and the other inducing the dyslocalization), these molecules are coupled by chemical methods, e.g. by introducing a polylinker. One great advantage of this screening method is that each molecule needs to bind only to the target molecule, but does not necessarily need also to influence the function of the target molecule.

In the following examples, a recombinant fusion protein was generated in order to direct the AML1-ETO repressor activity at promoters which are essential for the survival and the proliferation of myeloid cells. A high degree of specificity was achieved by various effects. The c-myb binding sites were used as target for GFP-M&M and AML1-ETO repressor complexes. C-myb is essential for hematopoietic cells but not for the development of other organs (Mucenski, 1991, Cell Vol. 65, pp. 677-89).

The essential significance of c-myb for cellular proliferations of leukemic cells is generally known. Inhibition of myb-dependent genes represents a substantial target of leukemia therapy (Mucenski, 1991, Cell Vol. 65, pp. 677-89;Ratajczak, 1992, Proc. Natl. Acad. Sci. USA, Vol. 89, pp. 118237; Gewirtz et al., 1988, Science, Vol. 242, pp. 1303-6;Gewirtz A. M., 1999, Oncogene, Vol. 18, 3056-62).

The experiments show that the dyslocalization molecule of the invention (in this case a recombinant fusion protein) is not toxic for cells which do not express AML1-ETO. A high specific toxicity was achieved for cells which had suffered tumor-inducing transformations.

a Representation of the FACS results for BrdU-positive apoptotic cells. The unshaded curves represent the apoptosis rate in the cells transfected with a empty vector for control purposes.

b Representation of the proportions of apoptotic cells in the transfected 32D cells.

Figure 7:
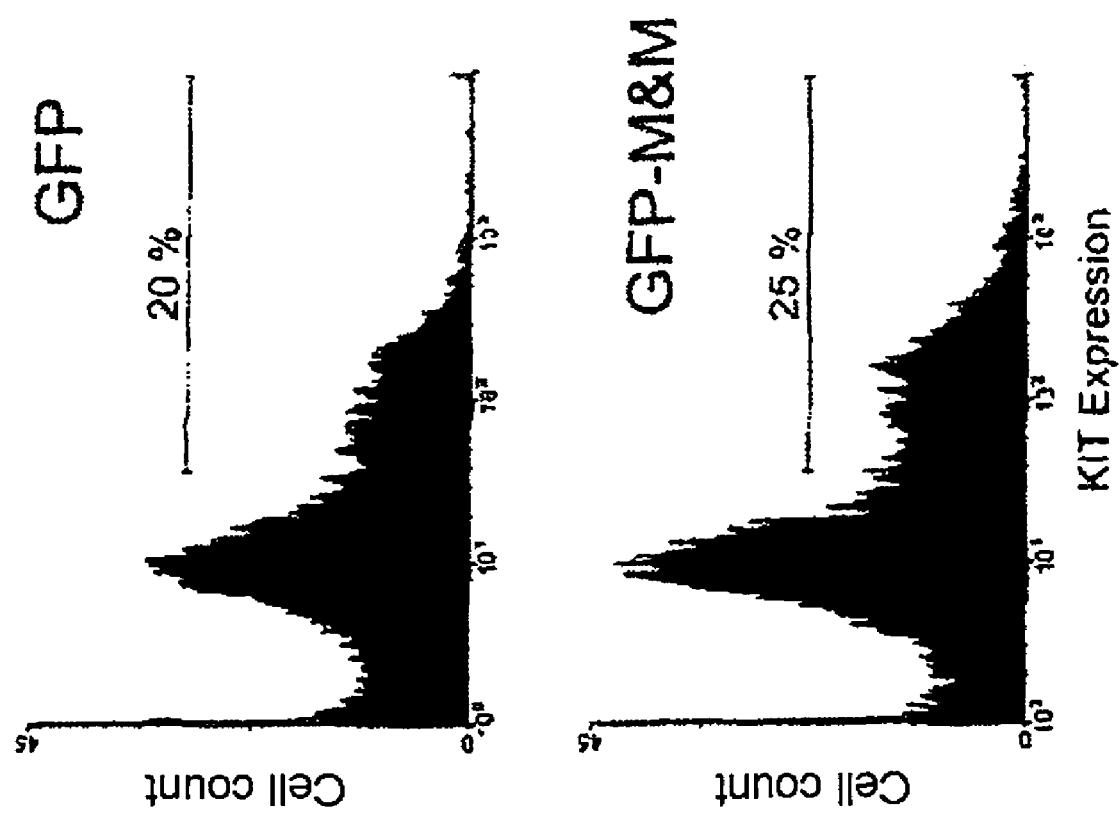

FIG. 7: In cells without AML1-ETO, MYB-dependent promoters are not repressed in vivo by GFP-M&M. Primary murine bone marrow cells were transduced with GFP or GFP-M&M. Subsequently, the expression of KIT in the GFP-positive cells was analyzed. The results of one of two experiments are shown.

MATERIAL AND METHODS

The following material and methods were used in the examples:

1. Plasmids:

The GFP-M&M expression plasmid in pcDNA3.1 was prepared by means of a PFU polymerase chain reaction (PCR) using a murine c-myb expression plasmid and cDNA from KCL22 cells as template, wherein specific primers for the DNA binding domain of c-myb (encoded by nucleotides 193-594 of SEQ ID NO:13;including the restriction sites for KpnI and BamHI) and the AML1 binding domain of MEF (encoded by nucleotides 251-618 of SEQ ID:12; including restriction sites for BamHI and EcORI) were used. The PCR products were cloned in reading direction into GFP-pcDNA3.1 (GFP corresponds to nucleotides 91-813 of SEQ ID NO:11). GFPΔM&M was cloned correspondingly, using a PCR fragment which lacked the first 159 base pairs of the DNA binding domain of c-Myb.

Primers for the AML1 Binding Domain of MEF:

MEF-BamH1 for:5'-ATA GGA TCC GCC ACC TCG CAC ACC ATG TCA-3' (SEQ ID NO: 3)

MEF-EcoR1 rev:5'-CAG AAT TCG CCT TTG CCA TCC TTT GAT TTC-3' (SEQ ID NO: 4)

Primers for the DNA Binding Domain of c-myb:

myb-Kpn1 for: 5'-CAG AGA GGT ACC GTC ATT GCC AAT TAT CTG-3' (SEQ ID NO: 5)

myb-BamH1 rev:5'-CAG AGA GGA TCC GTA GCC TTC CTG TTC CAC-3' (SEQ ID NO: 6)

The myb-TK (thymidine kinase) luciferase construct was a gift from Prof. Klempnauer. The AML1-ETO cDNA was subcloned into pcDNA3.1.

2. Cell lines and transfection:

The IL-3-dependent murine myeloid cell line 32Dc13, the human myeloid cell lines KC122 and Kasumi-1, and the monkey kidney cell line Cos7 were cultured by methods known in the art. 32Dc13 cells and KC122 cells were transfected with 15 µg of plasmid DNA by electroporation, and Cos cells were transfected with 5 µg of plasmid DMA using Lipofectamine (Invitrogen).

3. Immunoblotting:

Protein lysates were prepared from the Cos cells transfected with the expression vectors for GFP, GFP-M&M or GFP-ΔM&M. The three proteins were detected using the monoclonal murine GFP antibody (Clonetech, Heidelberg, Germany), detection taking place through incubation with radish, peroxidase conjugated secondary IgG antibodies against mouse IgG (Jackson ImmunoResearch).

4. Electrophoretic Mobility Shift Assay

Cos 7 cells were transfected with a total amount of 5 µg of the expression vectors for c-myb, AML1-ETO, GFP and GFP-M&M in various combinations. The preparation of cell nuclear extracts of the transfected Cos 7 cells, the binding reaction and the oligonucleotides which have the c-myb consensus binding sequence are described in Müller. et al., 1999, Blood, Vol. 94, pp. 4255-62. 100 ng of double-stranded oligonucleotides which had either the myb consensus site or a nonspecific binding site were used for the competitive experiments.

5. Chromatin Immunoprecipitation:

KCL22 cells were transfected with FLAG AML1-ETO and GFP or GFP-M&M. 12 hours after the transfection, the cellular proteins were bound to the DNA by adding 1% formaldehyde for 10 minutes, and then the reaction was stopped by adding 0.125 M glycine. The cells were washed twice in ice-cold PBS and lyzed in. 1 ml of RIPA lysis buffer with protease inhibitors, 200 µM sodium orthovanadate and 50 µM NaF. After incubation on ice for 10 minutes, the chromatin was fragmented by use of UV rays (9 pulses of 5 -seconds). The cell debris was removed by centrifugation, and 50 µl were stored as input control. The remainder of the lysate was prepurified in 40 µl of protein A/G agarose with 5 µg of rabbit and mouse IgG. The remainder of each lysate was divided into two samples, and the immunoprecipitation was carried out either using 3 µg of an anti-FLAG or mouse IgG with 40 µl of protein A/G agarose overnight. The immunocomplexes were washed eight times in a buffer with a low salt content (0.1% SDS, 150 µM NaCl, 1% Triton X-100, 2 µM EDTA, pH 8.0, 20 µM Tris-HCl, pH 8.1). The connections between the DNA and the proteins in the immune complexes and the input control were then redissolved, and the DNA was phenol/chloroform extracted from the solution. Subsequently, specific promoter sequences for the c-kit promoter region and the $p14^{ARF}$ promoter region were detected in the samples by means of PCR.

The PCR was carried out with a Taq, polymerase (Promega) on a Mastercycler (Eppendorf) (95° C. for 3 min., 37 cycles at 95° C. for 1 min., 60° C. for 1 min. and 72° C. for 1 min.). The products were separated on a 2% agarose gel and stained with ethidium bromide.

Primers for the $p14^{ARF}$ Promoter Region:

$p14^{ARF}$ for: 5'-AGT GGC TAC GTA AGA GTG ATC GC-3' (SEQ ID NO: 7)

$p14^{ARF}$ rev: 5'-CTT ACA GAT CAG ACG TCA AGC CC-3' (SEQ ID NO: 8)

Primers for the c-kit Promoter Region:

c-kit for: 5'- ACT GTT GTT GCT TTC CGT TCA A-3' (SEQ ID NO: 9)

c-kit rev: 5'- TTA AGC CCG ATT TCA CTG CC-3' (SEQ ID NO: 10)

6. Luciferase Detection:

The promoter activity was detected by methods known in the art (Müller et al., 2000, Mol. Cell. Biol., Vol. 20, pp. 3316-29). This entails a total amount of 15.5 µg of plasmid being transfected by electrophoresis. The mixture consisted of 5 µg of a myb-TK luciferase construct, 0.5 µg of PRL-null plasmid (Promega, Madison, Wis.) for internal standardization and 5 µg of the expression vectors for AML1, AML1-ETO, GFP-ΔM&M and GFP-M&M in various combinations. Empty vector was cotransfected to equalize the total amount of transfected DNA. After 18 hours, the cells were lyzed, and the activity of the firefly and renilla luciferase was detected using the dual luciferase assay system from Promega. The renilla luciferase activity, was used for internal standardization of the transfection efficiency. The mean values and standard errors were calculated from three independent experiments.

7. Clonal Growth in Methylcellulose:

32Dc13 cells and Kasumi cells were transiently transfected with a total amount of 15 g of the expression vectors for AML1, AML1-ETO, GFP, GFP-M&M and GFP M&M in various combinations. To investigate the clonal growth, the transfected cells were separated on the day following the electroporation by gradient centrifugation, and seeded in a concentration of $1\times10^5$ live cells per 35 mm plate in 1 ml of a culture mix. This mix consisted of Isocove modified Dulbecco medium (IMDM, Life Technologies, Grand Island, N.Y.), 1% methylcellulose, 20% FCS, IL-3 (1 ng/ml) and 0.6 mg/dl G418. All experiments were set up in triplicate, and the colonies were counted on day 10. Mean values and standard errors were calculated from three independent experiments (two experiments for Kasumi cells).

8. Apoptosis Assay:

32Dc13 cells were transiently transfected with the expression vectors for GFP, GFP-M&M and AML1-ETO in various combinations. After 24 hours, the GFP-positive cells were sorted out from the total cells by flow cytometry, and investigated further. The percentage of apoptotic cells among the GFP-positive cells was determined using a TUNEL assay (APO-BrdU kit from PharMingen), the experiments being carried out in accordance with the manufacturer's instructions. The results of one of these three independent experiments with similar results are shown.

9. Retroviral Transduction of Primary positive Bone Marrow Cells:

Bone marrow cells were removed from the femura of six month old BALB/c mice and cultivated in RPMI1640 medium with addition of murine IL-3. Phoenix cells were transiently transfected with GFP or GFP-M&M in MSCV2.2 using Lipofectamine Plus (Invitrogen). The medium was changed after 24 hours. 48 hours after the transfection, the supernatants were harvested, filtered (0.45 µm) and, after addition of 4 µg/ml Polybrene, added to the bone marrow cells. The cells were then centrifuged at 2000 g for 45 min and incubated at 37° C. for 2 hours and subsequently transduced a second time as described. Two further rounds of transduction were performed the next day.

24 hours after the end of the transduction, the expression of GFP and KIT (anti-CD117-PE from PharMingen) in the cells was investigated by flow cytometry, and apoptosis was investigated using Annexin V-PE (PharMingen) in accordance with the manufacturer's protocols.

EXAMPLE 1

Cloning of GFP-M&M and Expression in Cos Cells

A fusion protein composed of the enhanced green fluorescent protein (GFP, for detection purposes; encoded by nucleotides 91-813 of SEQ ID NO:11), of the DNA binding domain of murine c-myb (nucleotides 193-594 of SEQ ID NO:13 encode amino acid residues 65-198 of murine c-myb; cf. Sakura et al., 1989, Proc. Natl. Acad. Sci. USA, Vol. 86, pp. 5758-61) and of the AML1-binding domain of the human myeloid elf like factor, MEF (nucleotides 251-618 of SEQ ID:12 encode amino acid residues 87-206 of human MEF; cf. Mao S. et al., 1999, Mol. Cell. Biol., Vol. 19, pp. 3635-44)) was constructed.

The transcription factor c-myb is known to be essential for normal hematopoiesis and the survival of hematopoietic cells (Mucenski et al., 1991, Cell, Vol. 65, pp. 677-89). It was shown that inhibition of c-myb by antisense strategies or c-myb knock-out mice are unable to develop normal hematopoiesis (Ratajczak et al., 1992, Proc. Natl. Acad. Sci. USA, Vol. 8,9, pp. 11823-7).

Figure 1A:
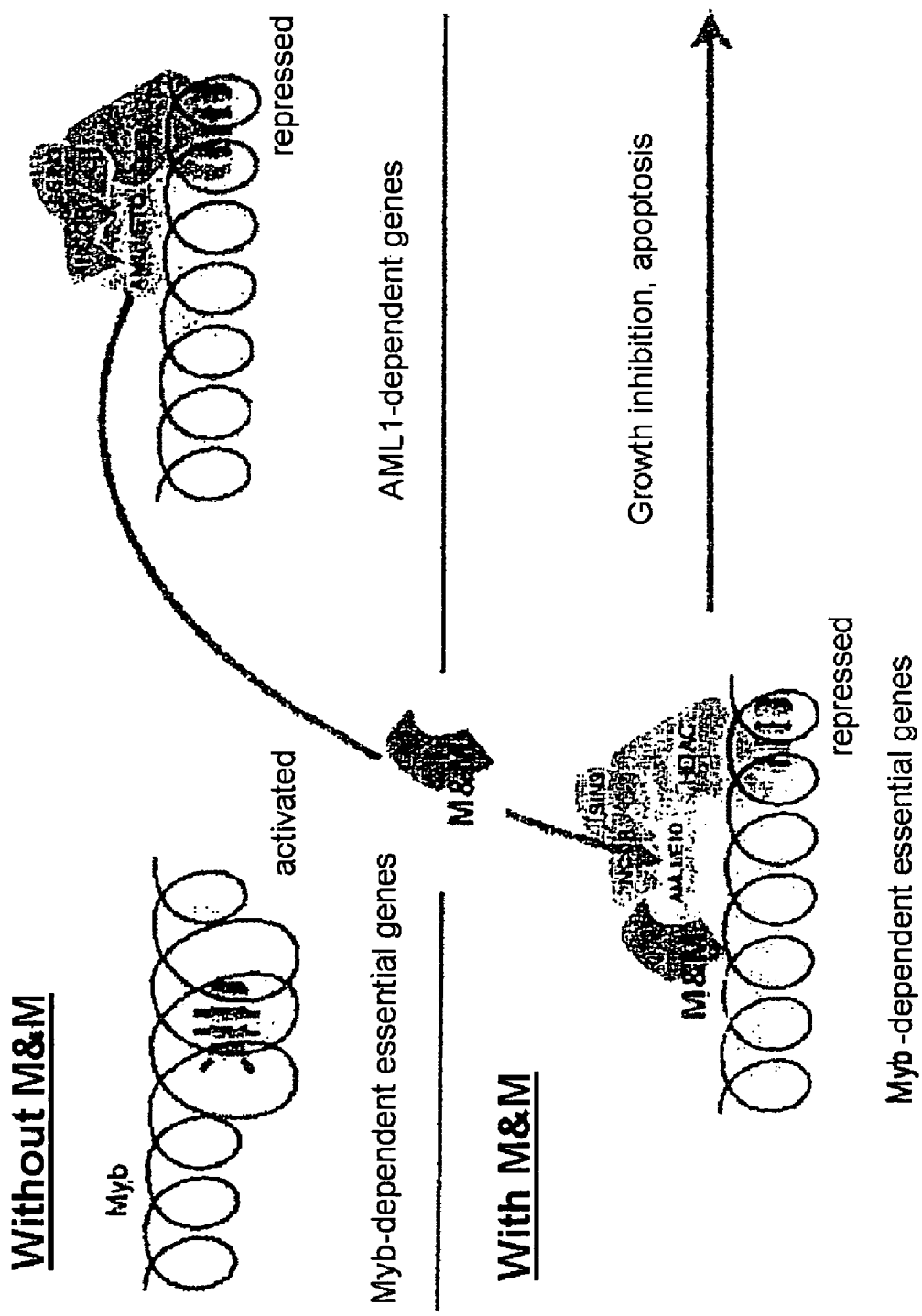
FIG. 1: Construction of an AML1-ETO dyslocalization protein
  a Hypothesis of the function of a chimeric protein consisting of the DNA binding domain of c-myb and the AML1 binding domain of MEF.
  b Structure of the chimeric protein and of the deletion mutant.
  c Immunoblotting detection from Cos7 cell lysates using an anti-GFP antibody after transfection of the cells with GFP, GFP-ΔM&M and GFP-M&M.
Figure 1B:
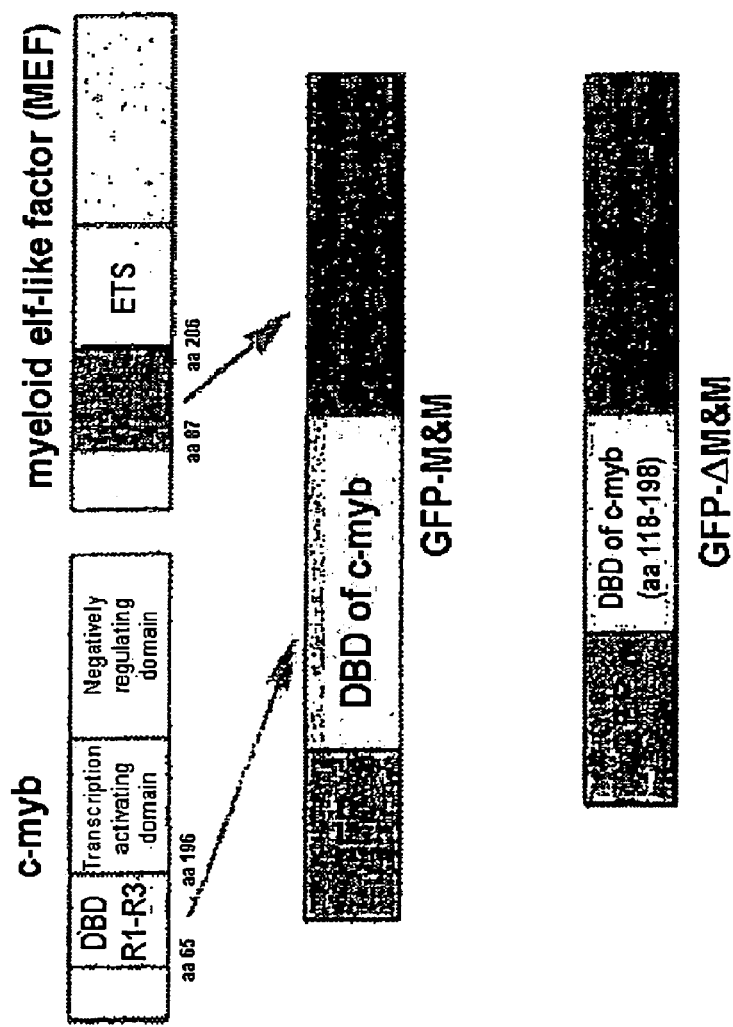

The AML1 binding domain of MEF (myeloid like ELF factor) was used as second part of the chimeric protein. Amino acids 87-206 of MEF bind strongly to AML1 and AML1-ETO in vivo and in vitro (Mao S. et al., 1999, Mol. Cell. Biol., Vol. 19, pp. 3635-44). All three domains were cloned in reading direction into the expression vector pcDNA3.1. This construct was referred to as GFP-M&M (FIG. 1b). A deletion mutant lacking the first 53 amino acids, of the DNA binding domain of c-myb was prepared for control purposes. The deletion mutant was referred to as GFP-M&M.

Figure 1C:
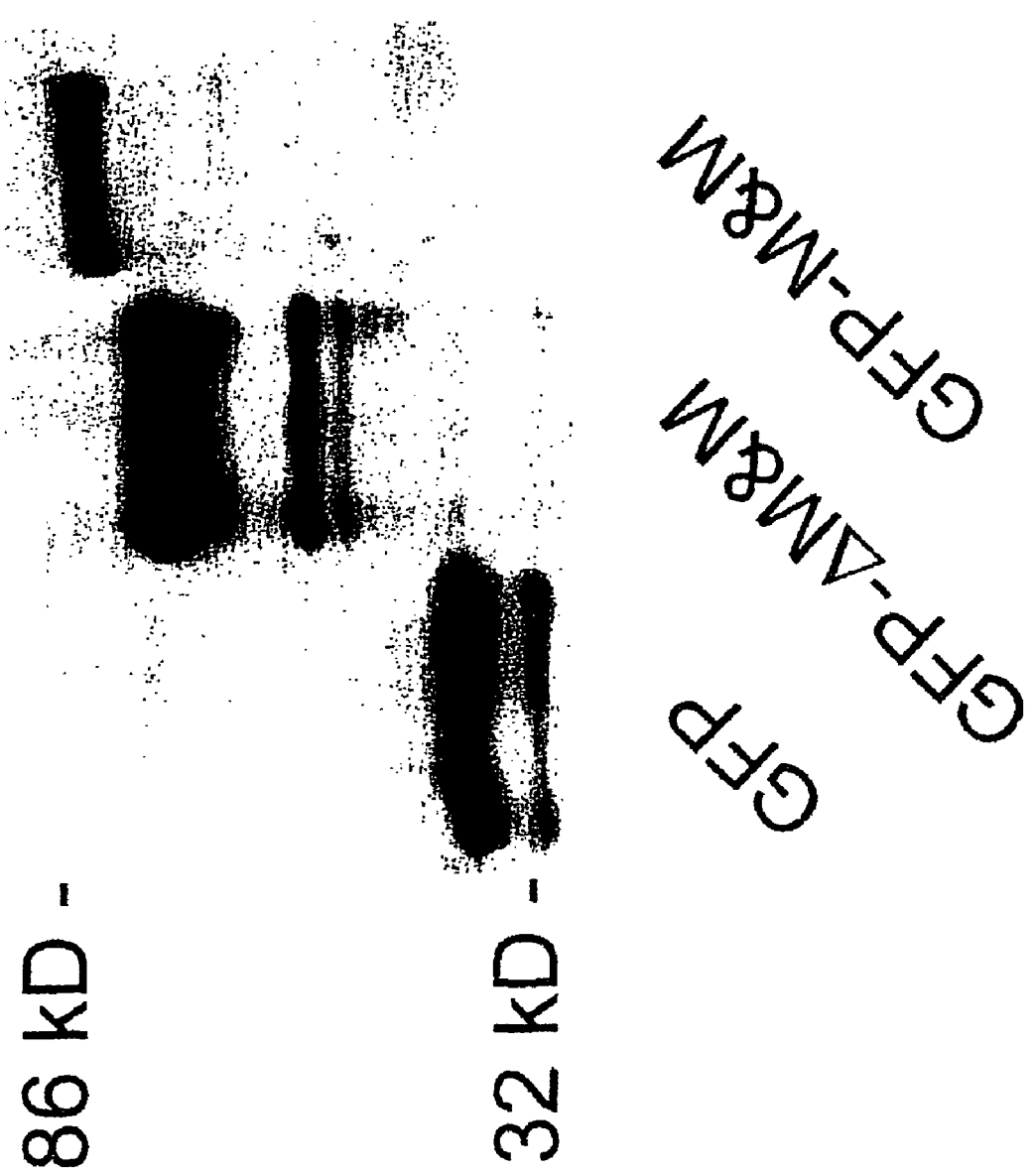

Expression of the recombinant proteins was analyzed after transient transfection in Cos-7 cells by means of immunoblotting detection methods using anti-GFP antibody (GFP alone 35 kDa, GFP-ΔM&M 80 kDa; GFP-M&M 85 kDa; FIG. 1 c).

EXAMPLE 2

Analysis of the Binding of GFP-M&M to myb Binding Sites

Figure 2:
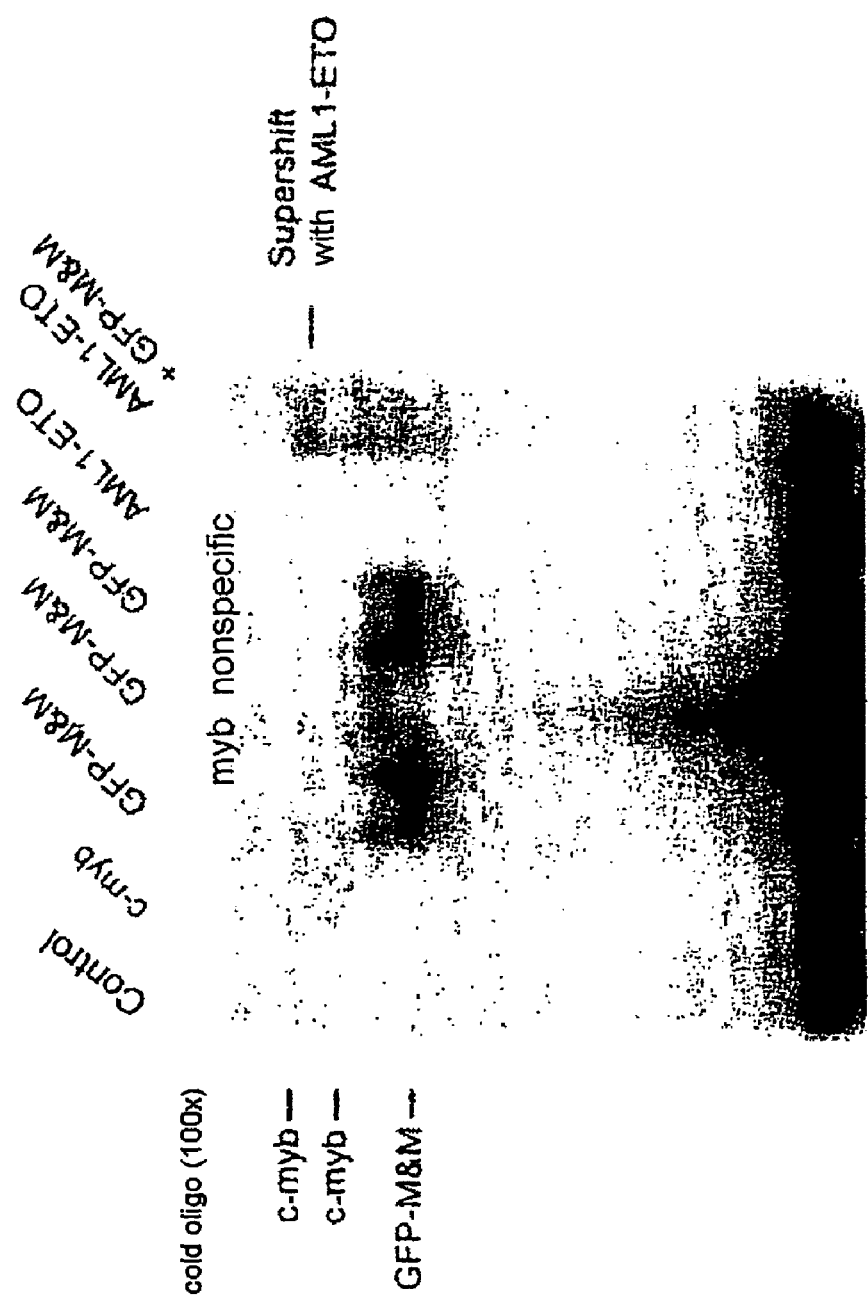
FIG. 2: Specific binding of GFP-M&M to myb binding sites and binding of AML1-ETO in vitro. Cell nuclear extracts of Cos 7 cells which had been transfected with c-myb GFP-M&M and AML1-ETO were analyzed in electrophoretic mobility shift assays (EMSA). Competition experiments with specific myb and nonspecific oligonucleotides show the specificity of GFP-M&M binding. The supershift of M&M produced by cotransfection of GFP-M&M with AML1-ETO shows the dyslocalization of AML1-ETO to the myb binding sites.

Electrophoretic mobility shift assays were carried out to analyze the interaction of GFP-M&M with myb DNA binding sites (cf. FIG. 2). For this purpose, nuclear extracts of transiently transfected Cos 7 cells were prepared. A double-stranded myb consensus oligonucleotide served as target DNA. These experiments showed that GFP-M&M, like c-myb, specifically binds to myb DNA binding sites. AML1-ETO alone showed no binding to the myb binding sites, but GFP-M&M led to binding of AML1-ETO to the DNA. This resulted in a supershift of the complex consisting of DNA, GFP-M&M and AML1-ETO (FIG. 2).

EXAMPLE 3

GFP-M&M Binds AML1-ETO to the Endogenous c-kit Promoter

Binding of GFP-M&M and binding of AML1-ETO to endogenous c-myb target promoters was analyzed using a chromatin immunoprecipitation detection method (ChiP) in KCL22 cells.

The c-kit promoter was chosen as c-myb dependent endogenous promoter. The demonstrated binding of AML1-ETO to the p14$^{ARF}$ promoter (Linggi et al., Nature Medicine, 8 (7), July 2002) was analyzed as positive control. A FLAG-labeled form of AML1-ETO was expressed in combination with GFP or GFP-M&M in KCL22 cells. The transcription factors were crosslinked with, DNA by using formaldehyde. After cell lysis and DNA fragmentation, the DNA/AML1-ETO complexes were immunoprecipitated by using an anti-FLAG antibody or, for control purposes, nonspecific antibodies. The crosslinking was abolished and the presence of the c-kit and p14$^{ARF}$ promoter DNA sequences was analyzed by PCR. The sequence of the c-kit promoter was undetectable in the ChIP samples of the KCL22 cells transfected with AML-ETO and GFP.

Figure 3:
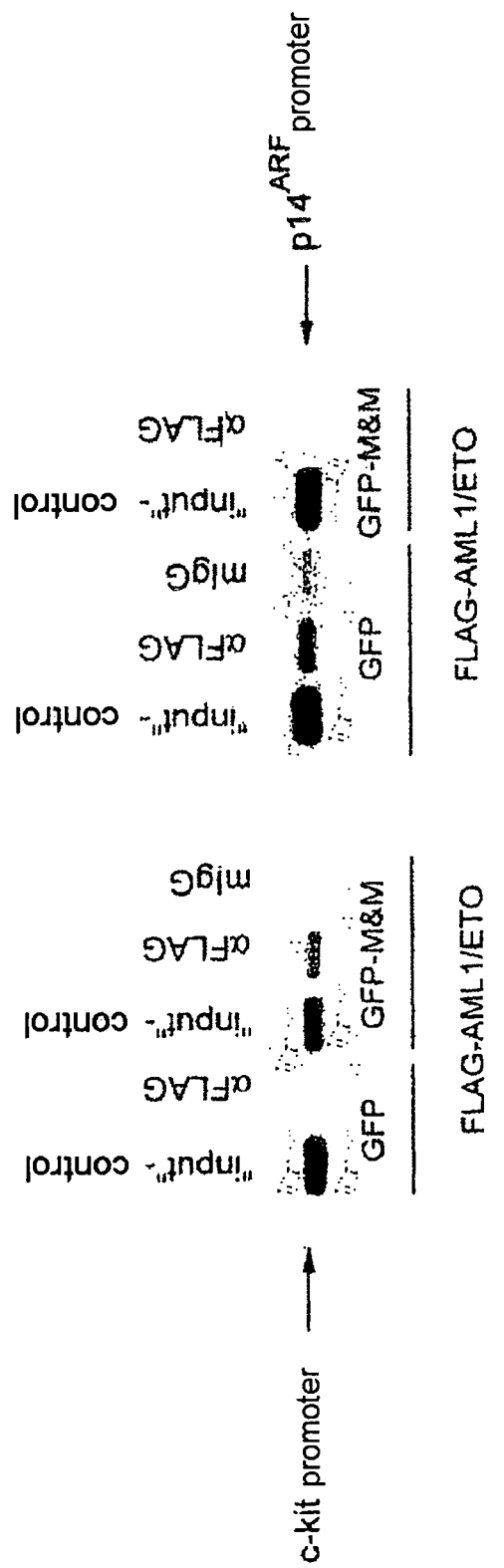
FIG. 3: Binding of AML1-ETO to the endogenous c-kit promoter by means of GFP-M&M. KCL22 cells were transfected with FLAG-AML1-ETO and GFP or GFP-M&M, DNA-binding proteins were firmly coupled to DNA by use of formaldehyde, the cells were lyzed, and the DNA was fragmented and immunoprecipitated with anti-FLAG or nonspecific antibodies. A PCR was used to detect the promoter sequences of c-kit and p14$^{ARF}$ in the immunoprecipitated chromatin. One representative of two experiments is shown.

However, in the presence of GFP-M&M, the c-kit promoter sequences were immunoprecipitated with AML1-ETO (FIG. 3). In contrast thereto, the p14$^{ARF}$ promoter sequence was detected in immune complexes from KCL22 cells transfected with AML1-ETO and GFP. The sequence was not detected in the presence of AML1-ETO and GFP-M&M (FIG. 3).

These results show that GFP-M&M is able to bind AML1-ETO to the endogenous c-myb dependent promoter c-kit in vivo.

EXAMPLE 4

Inhibition of myb Dependent Promoters in the Presence of GFP-M&M and AML1-ETO

GFP-M&M binds to myb dependent promoters, forms a complex with AML1-ETO (where present) and thus inhibits gene expression.

Figure 4:
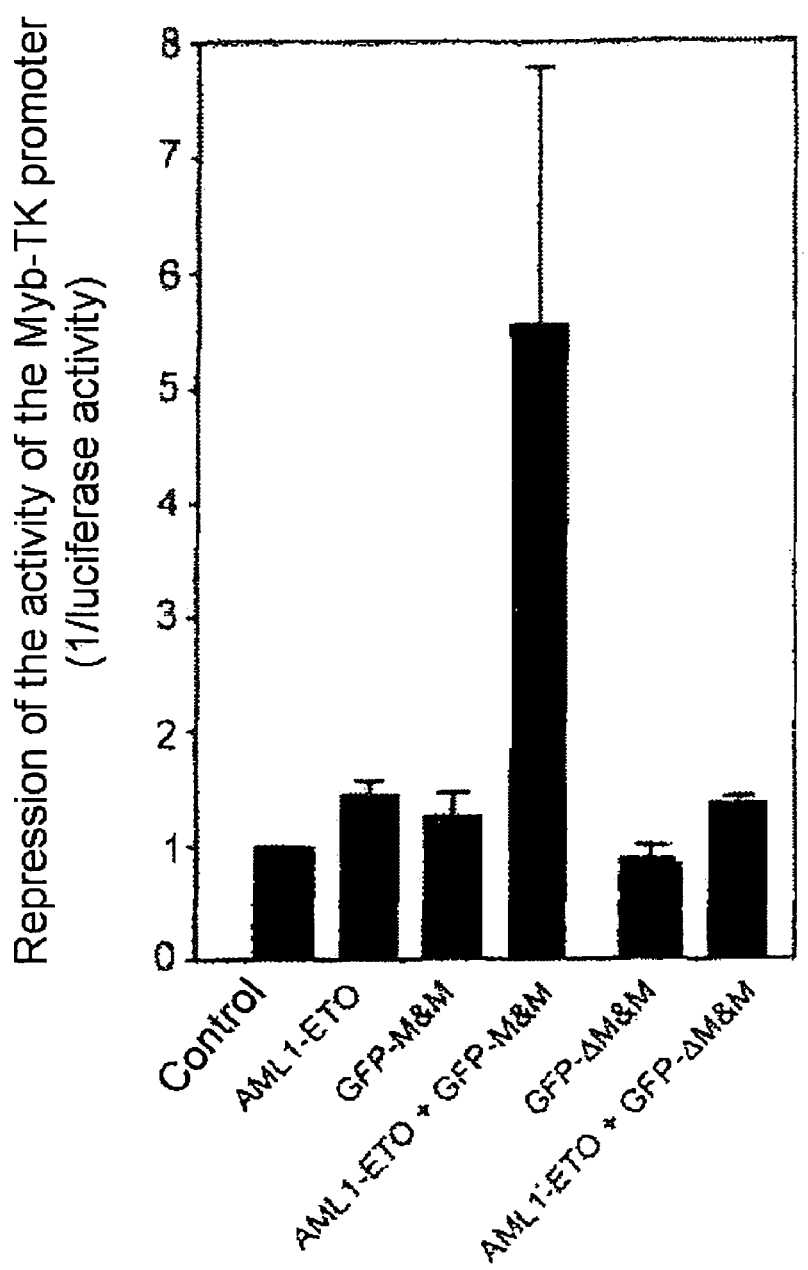
FIG. 4: Specific repression of the myb-dependent promoter by GFP-M&M in the presence of AML1-ETO. KCL22 cells were transiently transfected with a myb-dependent luciferase construct and c-myb, AML1, AML1-ETO, GFP-AM&M and GFP-M&M (as indicated). The mean value and the standard error of three independent experiments is depicted.

Luciferase assays were carried out as a further demonstration, the luciferase gene being under the control of a minimal thymidine kinase promoter with three additional myb DNA binding sites (Ziebold et al., 1997, Curr. Biol., Vol. 7, pp. 253-60). KCL22 cells were transfected with the reporter constructs and GFP, GFP-M&M and AML1-ETO in various combinations (FIG. 4) None of the proteins was able on its own to have a substantial influence on luciferase activity. Cells expressing GFP-M&M and AML1-ETO together did, however, show a more than 5-fold inhibition of promoter activity (FIG. 4). It was then analyzed whether the functional interaction between GFP-M&M and myb DNA binding sites was necessary for the inhibition of the luciferase activity by GFP-M&M in AML1-ETO positive cells. The mutation of the DNA binding site in GFP-ΔM&M inhibits the DNA binding of the recombinant protein, although expression of the protein is unchanged (FIG. 1b). Neither expression of GFP-AM&M alone nor expression of GFP-ΔM&M and AML1-ETO together inhibited luciferase activity.

These results show that GFP-M&M binding to the DNA is necessary for repression of the myb dependent gene in the presence of AML1-ETO (FIG. 4).

EXAMPLE 5

Inhibition of Colony Growth by GFP-M&M in AML1-ETO Expressing Cells

The activity of the transcription factor Myb and the expression of the myb dependent genes are essential for the growth and proliferation of hematopoietic cells (White et al., 2000, Oncogene, Vol. 19, pp. 1196-205). Therefore, the effect of GFP-M&M on the proliferation and survival rate of AML1-ETO-containing cells was analyzed.

Firstly, the ability of the transfected hematopoietic 32D cells to form colonies was investigated. Colony growth was not inhibited in cells transfected with AML1, GFP-M&M or AML1 and GFP-M&M.

Figure 5A:
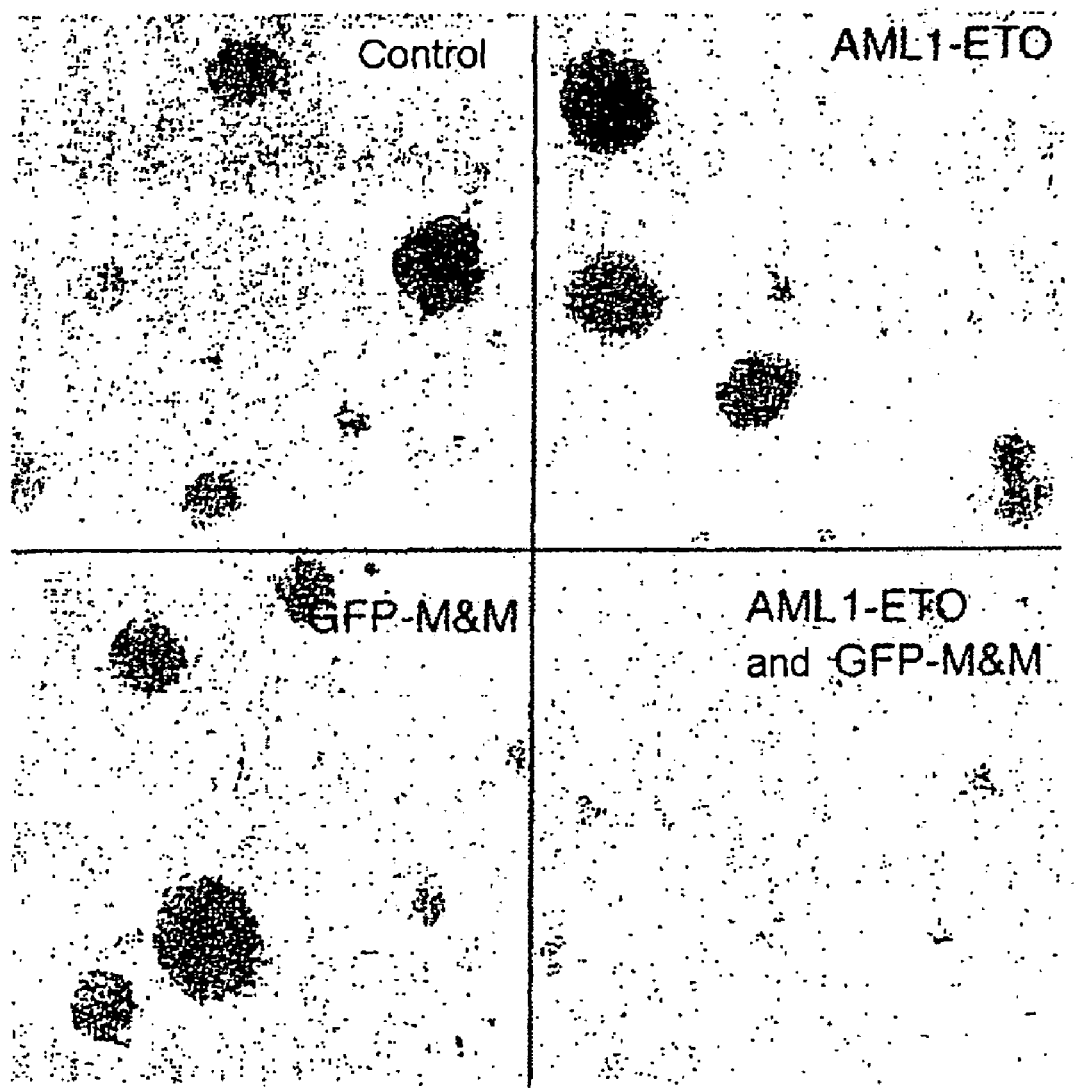
FIG. 5: GFP-M&M represses colony growth in AML1-ETO expressing cells.
  a 32D cells were transfected with GFP as control or AML1-ETO and GFP-M&M as indicated, and 1×10$^5$ cells were seeded in colony detection methods. The photographs show representative colonies on day 10.
  b 32D cells were transfected as indicated and seeded in the colony detection method. The colonies were counted on day 10. The repression of colony growth compared with the control transfection with GFP (set equal to 1) is depicted here. The mean value and the standard error of three independent experiments is shown.
  c AML1-ETO was transfected alone or in combination with GFP-M&M or GFP-ΔM&M into 32D cells and then seeded for colony detection methods. The mean value and the standard error of three independent experiments is depicted.
  d GFP or GFP-M&M were transfected- into Kasumi-1 cells which naturally express AML1-ETO, and seeded in colony detection methods. The mean value and the standard error of three independent experiments is depicted.
Figure 5B:
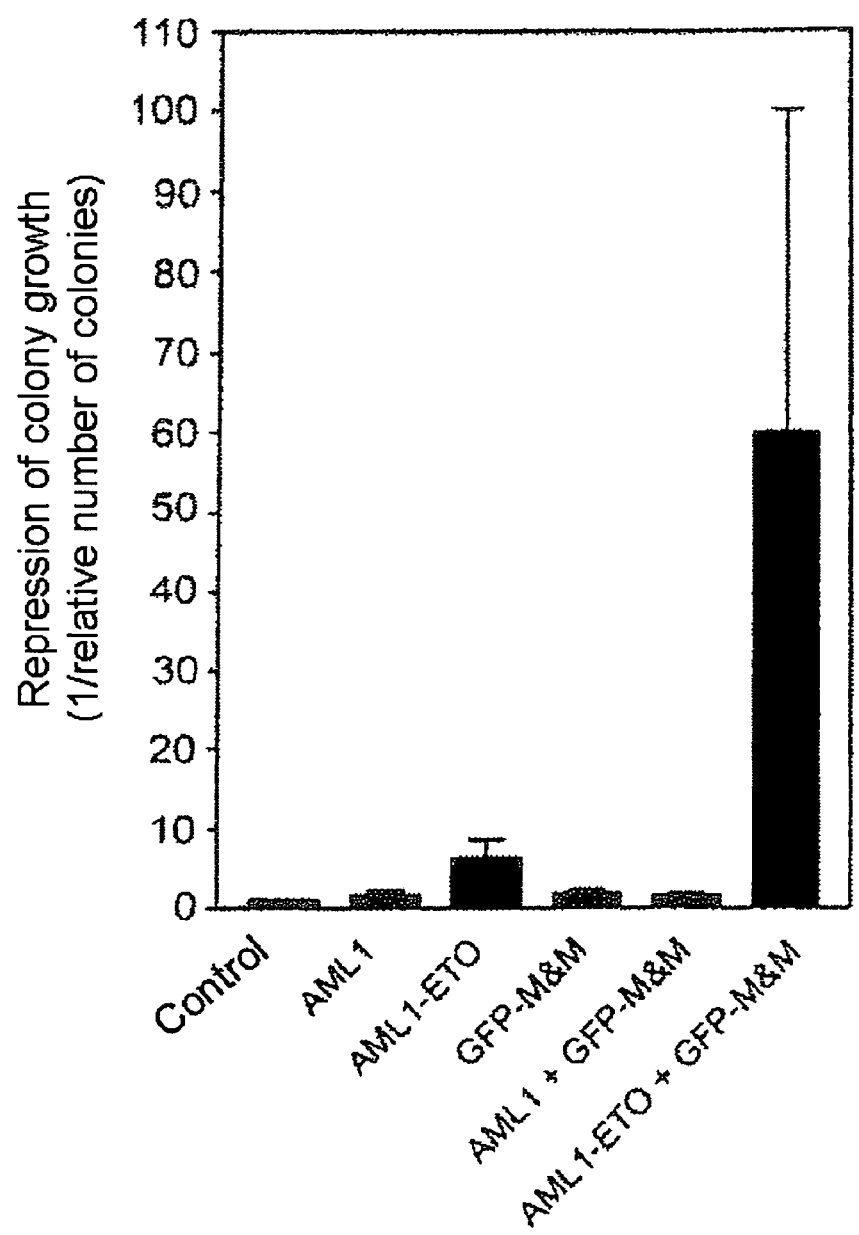
Figure 5C:
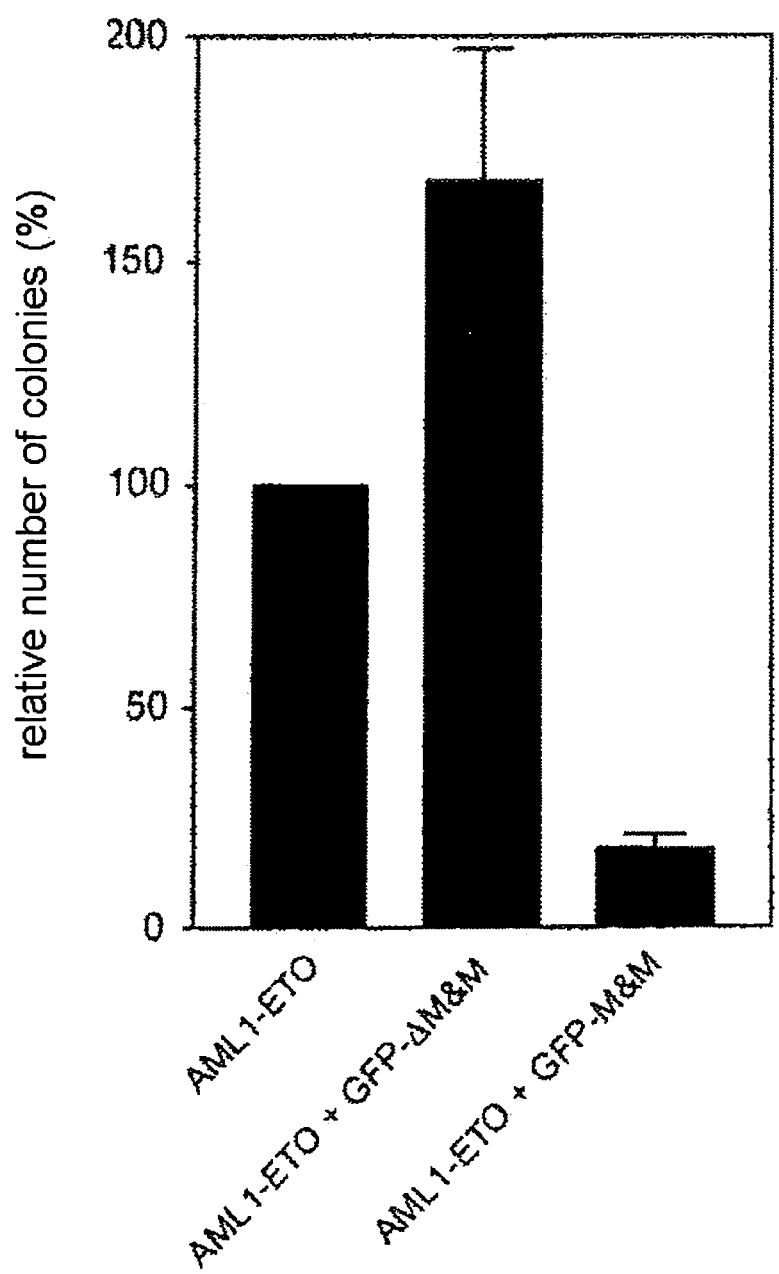

Cells transfected with AML1-ETO alone showed a six-fold inhibition of colony growth, which is probably attributable to the toxic effect of AML1-ETO itself (Muller et al., Mol. Cell. Bio., 2000, Vol. 20., pp. 3316-29). Transfection of the 32D cells with GFP-M&M in the presence of AML1-ETO did, however, reduce the growth of the colonies about 60-fold (FIG. 5a and 5b). In comparison to GFP-M&M and GFP-ΔM&M in colony assays it was found that coexpression of GFP-M&M and AML1-ETO reduced the relative number of colonies by more than 80%. In contrast thereto, GFP-ΔM&M and AML1-ETO did not inhibit colony growth (FIG. 5c). The latter observation shows that a functional interaction between GFP-M&M and myb DNA binding sites is necessary for inhibition of colony growth in AML-ETO positive cells.

Figure 5D:
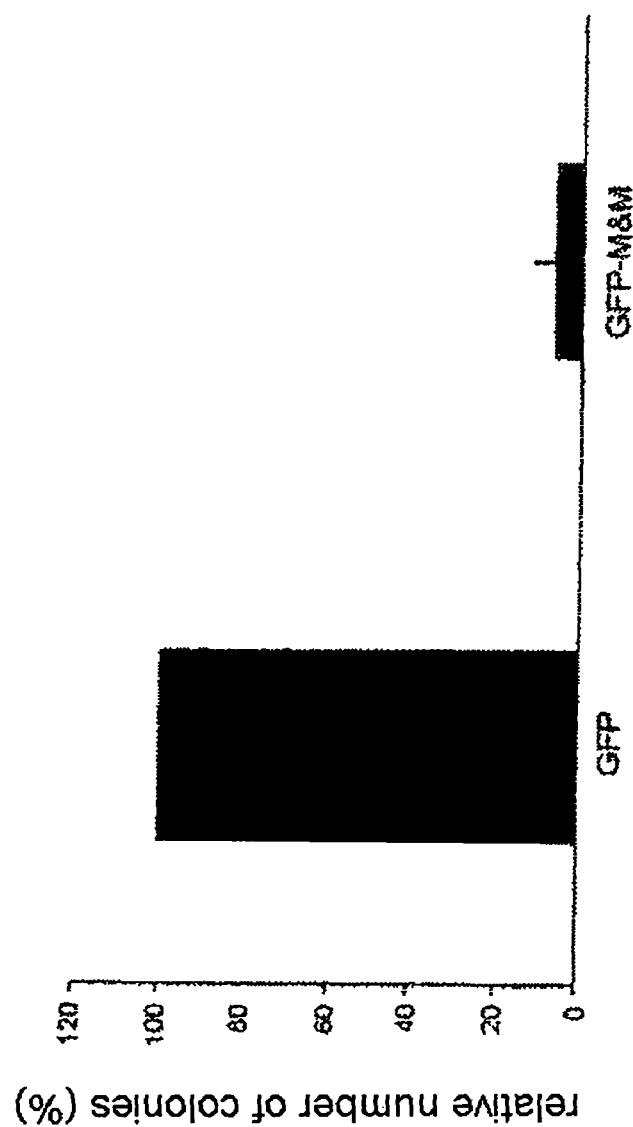

Besides the effects of GFP-M&M in AML1-ETO transfected cells, the activity of GRP-M&M in t(8;21) positive Kasumi-1 leukemia cells was also investigated. The colony growth was reduced twelve-fold (FIG. 5d) after transfection with GFP-M&M as compared to cells transfected with GFP-pcDNA3.1 alone (control).

EXAMPLE 6

Induction of Apoptosis by GFP-M&M in AML1-ETO-Containing Cells

Hematopoietic cells having no c-myb activity are subject to apoptosis (Taylor et al., 1996, Genes Dev., Vol 10, pp. 2732-44).

Figure 6A:
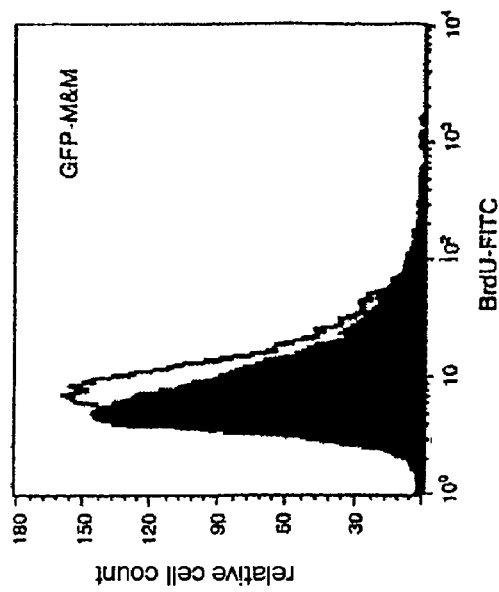
FIG. 6: GFP-M&M induces apoptotis in AML1-ETO expressing cells. 32D cells were transfected with AML1-ETO, GFP-M&M or both vectors and then the transfected cells were sorted by flow cytometry. The transfected cells were then analyzed in a TUNEL detection method.
Figure 6A:
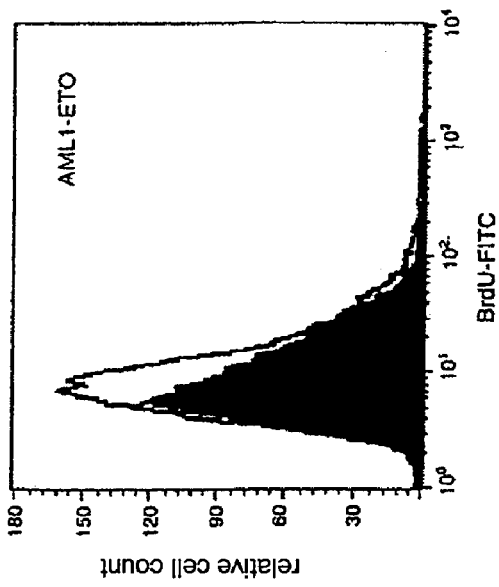
Figure 6A:
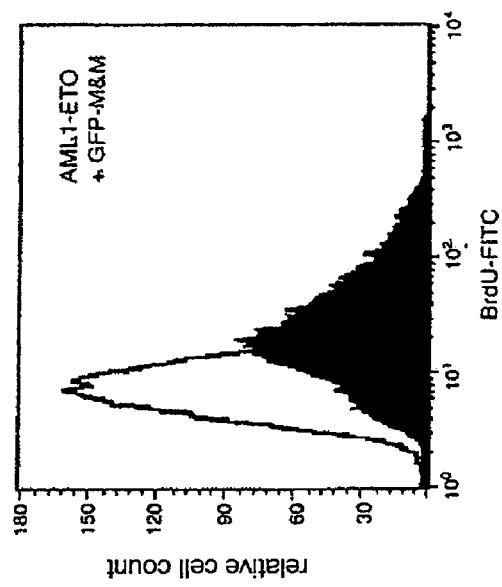
Figure 6B:
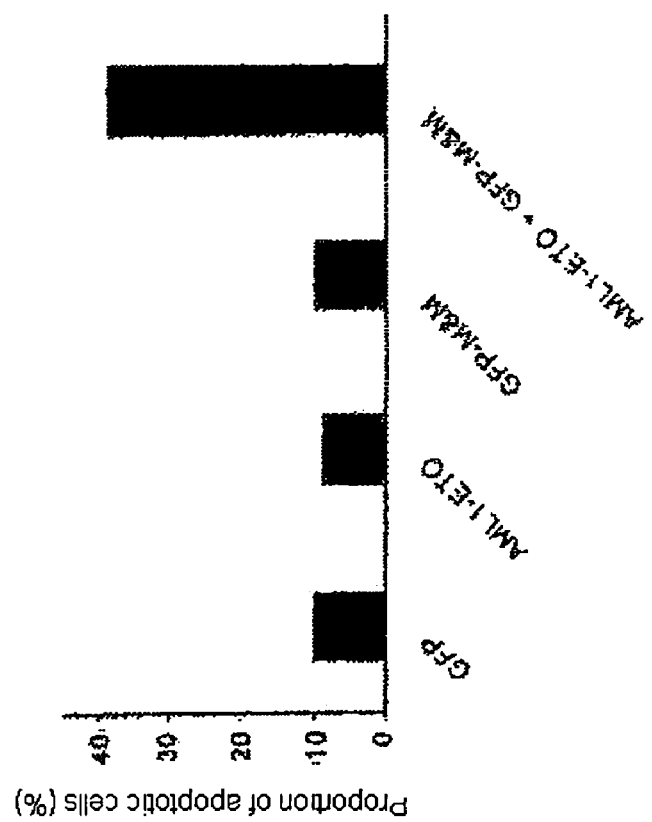

In order to investigate the effect of GFP-M&M in AML1-ETO positive cells and its influence on apoptosis, the presence of DNA strand breaks was investigated by a TUNEL assay. 32D cells were transfected with GFP, AML1-ETO or GFP-M&M or with a combination of AML1-ETO and GFP-M&M. After 24 hours, about 10% of the cells which expressed GFP, AML1-ETO or GFP-M&M alone were undergoing apoptosis. In contrast thereto, the percentage of apoptotic cells among the cells which expressed both AML1-ETO and GFP-M&M was 39%. This corresponds to a four-fold increase in the apoptosis rate (FIG. 6a and b).

EXAMPLE 7

MYB-Dependent Promoters are not Repressed in vivo by GFP-M&M in Cells without AML1-ETO In order to show that GFP-M&M does not repress MYB-dependent promoters in vivo in the absence of AML1-ETO, primary mouse bone marrow cells were subjected to retroviral transduction with GFP or GFP-M&M. This resulted in no significant difference in the expression of KIT (FIG. 7) and the rate of apoptosis in the GFP-positive cells. This shows that the compounds of the invention do not induce specific repression of the transcription of MYB-dependent promoters in healthy cells

The invention claimed is:

1. A recombinant fusion protein comprising a first binding domain and a second binding domain, wherein said first binding domain binds one molecule selected from the group consisting of AML1-ETO, BCR-Ab1, PML-RARalpha, PLZF-RARalpha, and EWS-FLI and said second binding domain effects dyslocalization of said molecule and binds the molecule to a nucleic acid sequence which regulates the transcription of a gene, wherein said first binding domain and said second binding domain are chimeric, and wherein said dyslocalization is to a site where said molecule is not normally present in tumor cells.

2. The fusion protein of claim 1, wherein the dyslocalization inhibits the growth of a tumor cell expressing said molecule.

3. The fusion protein of claim 1, wherein the dyslocalization induces apoptosis in a tumor cell expressing said molecule.

4. The fusion protein of claim 1, wherein the molecule affects survival of the tumor cell.

5. The fusion protein of claim 1, wherein the first binding domain has a binding affinity of $10^{-5}$M to $10^{-12}$M for said molecule.

6. The fusion protein of claim 1, wherein the first binding domain has a binding affinity of $10^{-7}$M to $10^{-9}$ M for said molecule.

7. The fusion protein of claim 1, wherein the molecule is not present in healthy cells or is present in another form relative to healthy cells.

8. The fusion protein of claim 1, wherein the fusion protein is purified.

9. The fusion protein of claim 1, wherein the molecule is AML1-ETO.

10. The fusion protein of claim 1, wherein the molecule comprises a DNA binding domain, a signal peptide, kinase activity, chromatin-modulatory properties, protein-protein interaction domains or transcriptional properties.

11. The fusion protein of claim 1, wherein said transcription is activated or inhibited.

12. The fusion protein of claim 1, wherein the second binding domain that effects dyslocalization comprises the peptide sequence of the c-myb DNA binding domain.

13. The fusion protein of claim 1, wherein the first binding domain comprises the peptide sequence of the AML-1 binding domain of the myeloid elf like factor.

14. The fusion protein of claim 1, wherein said second binding domain comprises the peptide sequence of the c-myb DNA binding domain and said first binding domain comprises the peptide sequence of the AML-1 binding domain of the myeloid elf like factor.

15. The fusion protein of claim 14, wherein the fusion protein has the sequence shown in SEQ ID NO: 1.

16. A method for the preparation of a fusion protein of claim 1, in which the fusion protein is recombinantly expressed or obtained by protein synthesis.

17. A method for preparing a pharmaceutical composition, comprising the steps of:
  (a) preparing a fusion protein according to the method of claim 16 and
  (b) formulating the fusion protein with a pharmaceutically acceptable carrier.

18. The fusion protein of claim 1, wherein said second binding domain to effect dyslocalization is a DNA binding domain.

19. A composition comprising the fusion protein of claim 1 in a pharmaceutically acceptable carrier.

* * * * *

SEQUENCE LISTING

<160> NUMBER OF SEQ ID NOS: 13

<210> SEQ ID NO 1
<211> LENGTH: 497
<212> TYPE: PRT
<213> ORGANISM: artificial sequence
<220> FEATURE:
<223> OTHER INFORMATION: Amino acid sequence of GFP-M&M

```
<400> SEQUENCE: 1

Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gly
225                 230                 235                 240

Thr Val Ile Ala Asn Tyr Leu Pro Asn Arg Thr Asp Val Gln Cys Gln
                245                 250                 255

His Arg Trp Gln Lys Val Leu Asn Pro Glu Leu Ile Lys Gly Pro Trp
            260                 265                 270

Thr Lys Glu Glu Asp Gln Arg Val Ile Glu Leu Val Gln Lys Tyr Gly
        275                 280                 285

Pro Lys Arg Trp Ser Val Ile Ala Lys His Leu Lys Gly Arg Ile Gly
290                 295                 300

Lys Gln Cys Arg Glu Arg Trp His Asn His Leu Asn Pro Glu Val Lys
305                 310                 315                 320

Lys Thr Ser Trp Thr Glu Glu Glu Asp Arg Ile Ile Tyr Gln Ala His
                325                 330                 335

Lys Arg Leu Gly Asn Arg Trp Ala Glu Ile Ala Lys Leu Leu Pro Gly
            340                 345                 350

Arg Thr Asp Asn Ala Ile Lys Asn His Trp Asn Ser Thr Met Arg Arg
        355                 360                 365

Lys Val Glu Gln Glu Gly Tyr Gly Ser Ala Thr Ser His Thr Met Ser
370                 375                 380

Thr Ala Glu Val Leu Leu Asn Met Glu Ser Pro Ser Asp Ile Leu Asp
385                 390                 395                 400

Glu Lys Gln Ile Phe Ser Thr Ser Glu Met Leu Pro Asp Ser Asp Pro
                405                 410                 415
```

```
Ala Pro Ala Val Thr Leu Pro Asn Tyr Leu Phe Pro Ala Ser Glu Pro
        420                 425                 430

Asp Ala Leu Asn Arg Ala Gly Asp Thr Ser Asp Gln Glu Gly His Ser
        435                 440                 445

Leu Glu Glu Lys Ala Ser Arg Glu Glu Ser Ala Lys Lys Thr Gly Lys
        450                 455                 460

Ser Lys Lys Arg Ile Arg Lys Thr Lys Gly Asn Arg Ser Thr Ser Pro
465                 470                 475                 480

Val Thr Asp Pro Ser Ile Pro Ile Arg Lys Lys Ser Lys Asp Gly Lys
                485                 490                 495

Gly

<210> SEQ ID NO 2
<211> LENGTH: 1491
<212> TYPE: DNA
<213> ORGANISM: artificial sequence
<220> FEATURE:
<223> OTHER INFORMATION: Nucleotide sequence of GFP-M&M

<400> SEQUENCE: 2
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgaccta cggcgtgcag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaagggt       720
accgtcattg ccaattatct gcccaaccgg acagatgtgc agtgccaaca ccggtggcag       780
aaagtgctga ccctgaact catcaaaggt ccctggacca agaagaaga tcagagagtc       840 atagagcttg tccagaaata tggtccgaag cgttggtctg ttattgccaa gcacttaaaa       900
gggagaattg gaaagcagtg tcgggagagg tggcacaacc atttgaatcc agaagttaag       960
aaaacctcct ggacagaaga ggaggacaga atcatttacc aggcacacaa gcgtctgggg      1020
aacagatggg cagagatcgc aaagctgctg cccggacgga ctgataatgc tatcaagaac      1080
cactggaatt ccaccatgcg tcgcaaggtg aacaggaag ctacggatc cgccacctcg      1140 cacaccatgt caaccgcgga agtcttactc aatatggagt ctcccagcga tatcctggat      1200
gagaagcaga tcttcagtac ctccgaaatg cttccagact cggaccctgc accagctgtc      1260
actctgccca actacctgtt tcctgcctct gagcccgatg ccctgaacag gcgggtgac       1320 actagtgacc aggagggca ttctctggag gagaaggcct ccagagagga aagtgccaag      1380
aagactggga atcaaagaa gagaatccgg aagaccaagg caaccgaag tacctcacct      1440 gtcactgacc ccagcatccc cattaggaag aaatcaaagg atggcaaagg c              1491
```

<210> SEQ ID NO 3
<211> LENGTH: 30
<212> TYPE: DNA
<213> ORGANISM: artificial sequence
<220> FEATURE:
<223> OTHER INFORMATION: Oligonucleotide primer MEF-BamHI for

<400> SEQUENCE: 3
ataggatccg ccacctcgca caccatgtca                              30

<210> SEQ ID NO 4
<211> LENGTH: 30
<212> TYPE: DNA
<213> ORGANISM: artificial sequence
<220> FEATURE:
<223> OTHER INFORMATION: Oligonucleotide primer MEF-EcoRI rev

<400> SEQUENCE: 4
cagaattcgc ctttgccatc ctttgatttc                              30

<210> SEQ ID NO 5
<211> LENGTH: 30
<212> TYPE: DNA
<213> ORGANISM: artificial sequence
<220> FEATURE:
<223> OTHER INFORMATION: Oligonucleotide primer myb-KpnI for

<400> SEQUENCE: 5
cagagaggta ccgtcattgc caattatctg                              30

<210> SEQ ID NO 6
<211> LENGTH: 30
<212> TYPE: DNA
<213> ORGANISM: artificial sequence
<220> FEATURE:
<223> OTHER INFORMATION: Oligonucleotide primer myb-BamHI rev

<400> SEQUENCE: 6
cagagaggat ccgtagcctt cctgttccac                              30

<210> SEQ ID NO 7
<211> LENGTH: 23
<212> TYPE: DNA
<213> ORGANISM: artificial sequence
<220> FEATURE:
<223> OTHER INFORMATION: Oligonucleotide primer p14ARFfor

<400> SEQUENCE: 7
agtggctacg taagagtgat cgc                                     23

<210> SEQ ID NO 8
<211> LENGTH: 23
<212> TYPE: DNA
<213> ORGANISM: artificial sequence
<220> FEATURE:
<223> OTHER INFORMATION: Oligonucleotide primer p14ARFrev

<400> SEQUENCE: 8
cttacagatc agacgtcaag ccc                                     23

<210> SEQ ID NO 9
<211> LENGTH: 22
<212> TYPE: DNA
<213> ORGANISM: artificial sequence
<220> FEATURE:
<223> OTHER INFORMATION: Oligonucleotide primer c-kit for

```
<400> SEQUENCE: 9
actgttgttg ctttccgttc aa                                             22

<210> SEQ ID NO 10
<211> LENGTH: 20
<212> TYPE: DNA
<213> ORGANISM: artificial sequence
<220> FEATURE:
<223> OTHER INFORMATION: Oligonucleotide primer c-kit rev

<400> SEQUENCE: 10
ttaagcccga tttcactgcc                                                20

<210> SEQ ID NO 11
<211> LENGTH: 4151
<212> TYPE: DNA
<213> ORGANISM: artificial sequence
<220> FEATURE:
<223> OTHER INFORMATION: cDNA EGFP

<400> SEQUENCE: 11
tagttattac tagcgctacc ggactcagat ctcgagctca agcttcgaat tctgcagtcg     60
acggtaccgc gggcccggga tccaccggtc gccaccatgg tgagcaaggg cgaggagctg    120
ttcaccgggg tggtgcccat cctggtcgag ctggacggcg acgtaaacgg ccacaagttc    180
agcgtgtccg gcgagggcga gggcgatgcc acctacggca agctgaccct gaagttcatc    240
tgcaccaccg gcaagctgcc cgtgccctgg cccaccctcg tgaccaccct gacctacggc    300
gtgcagtgct tcagccgcta ccccgaccac atgaagcagc acgacttctt caagtccgcc    360
atgcccgaag gctacgtcca ggagcgcacc atcttcttca aggacgacgg caactacaag    420
acccgcgccg aggtgaagtt cgagggcgac accctggtga accgcatcga gctgaagggc    480
atcgacttca aggaggacgg caacatcctg gggcacaagc tggagtacaa ctacaacagc    540
cacaacgtct atatcatggc cgacaagcag aagaacggca tcaaggtgaa cttcaagatc    600
cgccacaaca tcgaggacgg cagcgtgcag ctcgccgacc actaccagca gaacaccccc    660
atcggcgacg gccccgtgct gctgcccgac aaccactacc tgagcaccca gtccgccctg    720
agcaaagacc ccaacgagaa gcgcgatcac atggtcctgc tggagttcgt gaccgccgcc    780
gggatcactc tcggcatgga cgagctgtac aagtaaagcg gccgcgactc tagatcataa    840
tcagccatac cacatttgta gaggttttac ttgctttaaa aaacctccca cacctccccc    900
tgaacctgaa acataaaatg aatgcaattg ttgttgttaa cttgtttatt gcagcttata    960
atggttacaa ataaagcaat agcatcacaa atttcacaaa taaagcattt ttttcactgc   1020
attctagttg tggtttgtcc aaactcatca atgtatctta aggcgtaaat tgtaagcgtt   1080
aatattttgt taaaattcgc gttaaatttt tgttaaatca gctcattttt taaccaatag   1140
gccgaaatcg gcaaaatccc ttataaatca aagaataga ccgagatagg gttgagtgtt   1200
gttccagttt ggaacaagag tccactatta agaacgtgg actccaacgt caagggcga   1260 aaaaccgtct atcagggcga tggcccacta cgtgaaccat caccctaatc aagttttttg   1320
gggtcgaggt gccgtaaagc actaaatcgg aaccctaaag ggagccccg atttagagct   1380 tgacggggaa agccggcgaa cgtggcgaga aggaaggga agaaagcgaa aggagcgggc   1440 gctaggcgc tggcaagtgt agcggtcacg ctgcgcgtaa ccaccacacc cgccgcgctt   1500
aatgcgccgc tacagggcgc gtcaggtggc acttttcggg gaaatgtgcg cggaacccct   1560
atttgtttat ttttctaaat acattcaaat atgtatccgc tcatgagaca ataaccctga   1620
```

```
taaatgcttc aataatattg aaaaaggaag agtcctgagg cggaaagaac cagctgtgga   1680
atgtgtgtca gttagggtgt ggaaagtccc caggctcccc agcaggcaga agtatgcaaa   1740
gcatgcatct caattagtca gcaaccaggt gtggaaagtc cccaggctcc ccagcaggca   1800
gaagtatgca aagcatgcat ctcaattagt cagcaaccat agtcccgccc ctaactccgc   1860
ccatcccgcc cctaactccg cccagttccg cccattctcc gccccatggc tgactaattt   1920
tttttatttta tgcagaggcc gaggccgcct cggcctctga gctattccag aagtagtgag   1980
gaggcttttt tggaggccta ggcttttgca aagatcgatc aagagacagg atgaggatcg   2040
tttcgcatga ttgaacaaga tggattgcac gcaggttctc cggccgcttg ggtggagagg   2100
ctattcggct atgactgggc acaacagaca atcggctgct ctgatgccgc cgtgttccgg   2160
ctgtcagcgc aggggcgccc ggttcttttt gtcaagaccg acctgtccgg tgccctgaat   2220
gaactgcaag acgaggcagc gcggctatcg tggctggcca cgacgggcgt tccttgcgca   2280
gctgtgctcg acgttgtcac tgaagcggga agggactggc tgctattggg cgaagtgccg   2340
gggcaggatc tcctgtcatc tcaccttgct cctgccgaga agtatccat catggctgat   2400
gcaatgcggc ggctgcatac gcttgatccg gctacctgcc cattcgacca ccaagcgaaa   2460
catcgcatcg agcgagcacg tactcggatg aagccggtc ttgtcgatca ggatgatctg   2520
gacgaagagc atcaggggct cgcgccagcc gaactgttcg ccaggctcaa ggcgagcatg   2580
cccgacggcg aggatctcgt cgtgacccat ggcgatgcct gcttgccgaa tatcatggtg   2640
gaaaatggcc gcttttctgg attcatcgac tgtggccgc tgggtgtggc ggaccgctat   2700
caggacatag cgttggctac ccgtgatatt gctgaagagc ttggcggcga atgggctgac   2760
cgcttcctcg tgctttacgg tatcgccgct cccgattcgc agcgcatcgc cttctatcgc   2820
cttcttgacg agttcttctg agcgggactc tggggttcga aatgaccgac caagcgacgc   2880
ccaacctgcc atcacgagat ttcgattcca ccgccgcctt ctatgaaagg ttgggcttcg   2940
gaatcgtttt ccgggacgcc ggctggatga tcctccagcg cggggatctc atgctggagt   3000
tcttcgccca ccctaggggg aggctaactg aaacacggaa ggagacaata ccggaaggaa   3060
cccgcgctat gacggcaata aaaagacaga ataaaacgca cggtgttggg tcgtttgttc   3120
ataaacgcgg ggttcggtcc cagggctggc actctgtcga taccccaccg agaccccatt   3180
ggggccaata cgcccgcgtt tcttcctttt ccccacccca cccccaagt tcgggtgaag   3240
gcccagggct cgcagccaac gtcggggcgg caggccctgc catagcctca ggttactcat   3300
atatacttta gattgattta aaacttcatt tttaatttaa aaggatctag gtgaagatcc   3360
tttttgataa tctcatgacc aaaatccctt aacgtgagtt ttcgttccac tgagcgtcag   3420
accccgtaga aaagatcaaa ggatcttctt gagatccttt ttttctgcgc gtaatctgct   3480
gcttgcaaac aaaaaaacca ccgctaccag cggtggtttg tttgccggat caagagctac   3540
caactctttt tccgaaggta actggcttca gcagagcgca gataccaaat actgtccttc   3600
tagtgtagcc gtagttaggc caccacttca agaactctgt agcaccgcct acatacctcg   3660
ctctgctaat cctgttacca gtggctgctg ccagtggcga taagtcgtgt cttaccgggt   3720
tggactcaag acgatagtta ccggataagg cgcagcggtc gggctgaacg ggggggttcgt   3780
gcacacagcc cagcttggag cgaacgacct acaccgaact gagatacccta cagcgtgagc   3840
tatgagaaag cgccacgctt cccgaaggga gaaggcgga caggtatccg gtaagcggca   3900
gggtcggaac aggagagcgc acgagggagc ttccagggg aaacgcctgg tatctttata   3960
gtcctgtcgg gtttcgccac ctctgacttg agcgtcgatt tttgtgatgc tcgtcagggg   4020
```

```
ggcggagcct atggaaaaac gccagcaacg cggcctttt  acggttcctg gccttttgct    4080
ggccttttgc tcacatgttc tttcctgcgt tatccctga  ttctgtggat aaccgtatta    4140
ccgccatgca t                                                        4151

<210> SEQ ID NO 12
<211> LENGTH: 1992
<212> TYPE: DNA
<213> ORGANISM: Homo sapiens
<220> FEATURE:
<223> OTHER INFORMATION: cDNA MEF

<400> SEQUENCE: 12
atggctatta ccctacagcc cagtgacctg atctttgagt tcgcaagcaa cgggatggat      60
gatgatatcc accagctgga agacccctct gtgttcccag ctgtgatcgt ggagcaggta     120
ccctaccctg atttactgca tctgtactcg ggactggagt tggacgacgt tcacaatggc     180
atcataacag acgggacctt gtgcatgacc caggatcaga tcctggaagg cagttttttg     240
ctgacagatg acaatgaggc cacctcgcac accatgtcaa ccgcggaagt cttactcaat     300
atggagtctc ccagcgatat cctggatgag aagcagatct tcagtacctc cgaaatgctt     360
ccagactcgg accctgcacc agctgtcact ctgcccaact acctgtttcc tgcctctgag     420
cccgatgccc tgaacagggc gggtgacact agtgaccagg aggggcattc tctggaggag     480
aaggcctcca gagaggaaag tgccaagaag actgggaaat caaagaagag aatccggaag     540
accaagggca accgaagtac ctcacctgtc actgacccca gcatccccat taggaagaaa     600
tcaaaggatg gcaaaggcag caccatctat ctgtgggagt tcctcctggc tcttctgcaa     660
gacagaaaca cctgtcccaa gtacatcaag tggaccagc gagagaaagg catcttcaaa    720
ctggtggact ccaaagctgt gtccaagctg tggggaagc agaaaaacaa gcctgacatg     780
aactatgaga caatggggcg ggcactaaga tactactacc aaagaggcat actggccaaa     840
gtggaagggc agaggctggt gtaccagttt aaggagatgc caaggacct  ggtggtcatt     900 gaagatgagg atgagagcag cgaagccaca gcagccccac ctcaggcctc cacgcctct     960 gtggcctctg ccagtaccac ccggcgaacc agctccaggg tctcatccag atctgccccc    1020
cagggcaagg gcagctcttc ttgggagaag ccaaaaattc agcatgtcgg tctccagcca    1080
tctgcgagtc tggaattggg accgtcgcta gacgaggaga tccccactac ctccaccatg    1140
ctcgtctctc cagcagaggg ccaggtcaag ctcaccaaag ctgtgagtgc atcttcagtg    1200
cccagcaaca tccacctagg agtggccccc gtgggtcgg  gctcggccct gaccctgcag    1260
acgatcccac tgaccacggt gctgaccaat gggcctcctg ccagtactac tgctcccact    1320
cagctcgttc tccagagtgt tccagcggcc tctactttca aggacacctt cactttgcag    1380 gcctcttcc  ccctgaacgc cagttccaa  acagccagg tggcagcccc aggggctcca    1440
ctgattctca gtggcctccc ccaacttctg gctggggcca accgtccgac caacccggcg    1500
ccacccacgg tcacaggggc tggaccagca gggcccagct tcagccccc  tgggactgtc    1560 attgctgcct tcatcaggac ttctggcact acagcagccc ctagggtcaa ggaggggcca    1620
ctgaggtcct cctcctatgt tcagggtatg gtgacggggg ccccatggac ggggctgctg    1680
gttcctgaag agaccctgag ggagctcctg agagatcagg ctcatcttca gccacttcca    1740
acccaggtgg tttccagggg ttcccacaat ccgagccttc tggcaaccca gactttgtct    1800
cctcccagcc gccccactgt tgggctgacc ccagtggctg aacttgagct ctcctcaggc    1860
tcagggtccc tgctgatggc tgagcctagt gtgaccacat ctgggagcct tctgacaaga    1920
```

| | |
|---|---|
| tcccccaccc cagcccctttt ctccccattc aaccctactt ccctcattaa gatggagccc | 1980 |
| catgacatat aa | 1992 |

<210> SEQ ID NO 13
<211> LENGTH: 1913
<212> TYPE: DNA
<213> ORGANISM: Mus musculus
<220> FEATURE:
<223> OTHER INFORMATION: cDNA c-myb

<400> SEQUENCE: 13

| | |
|---|---|
| atggcccgga gaccccgaca cagcatctac agtagcgatg aagatgatga agacattgag | 60 |
| atgtgtgacc atgactacga tgggctgctg cccaaatctg gaaagcgtca cttggggaaa | 120 |
| actaggtgga caagggaaga ggatgagaag ctgaagaagc tggtggaaca gaacggaaca | 180 |
| gacgactgga agtcattgc caattatctg cccaaccgga cagatgtgca gtgccaacac | 240 |
| cggtggcaga aagtgctgaa ccctgaactc atcaaaggtc cctggaccaa gaagaagat | 300 |
| cagagagtca tagagcttgt ccagaaatat ggtccgaagc gttggtctgt tattgccaag | 360 |
| cacttaaaag ggagaattgg aaagcagtgt cgggagaggg ggcacaacca tttgaatcca | 420 |
| gaagttaaga aaacctcctg gacagaagag gaggacagaa tcatttacca ggcacacaag | 480 |
| cgtctgggga cagatgggc agagatcgca agctgctgc ccggacggac tgataatgct | 540 |
| atcaagaacc actggaattc caccatgcgt cgcaaggtgg aacaggaagg ctacctgcag | 600 |
| aagccttcca agccagcca gacgccagtg ccacgagct tccagaagaa caatcatttg | 660 |
| atggggtttg gcatgcctc acctccatct cagctctctc caagtggcca gtcctccgtc | 720 |
| aacagcgaat atcccctatta ccacatcgcc gaagcacaaa acatctccag tcacgttccc | 780 |
| tatcctgtcg cattgcatgt taatatagtc aacgtccctc agccggctgc ggcagccatc | 840 |
| cagagacact ataacgacga agaccctgag aaggaaaagc gaataaagga gctggagttg | 900 |
| ctcctgatgt caacagagaa cgagctgaag ggacagcagg cattaccaac acagaaccac | 960 |
| acttgcagct accccgggtg gcacagcacc tccattgtgg accagaccag acctcatggg | 1020 |
| gatagtgcac ctgtttcctg tttgggagaa caccatgcca ccccatctct gcctgcagat | 1080 |
| cccggctccc tacctgaaga agtgcctca ccagcaaggt gcatgatcgt ccaccagggc | 1140 |
| accattctgg acaatgttaa gaacctctta gaatttgcag aaacactcca gtttatagat | 1200 |
| tctttcttga acacttccag caaccatgaa aactcgggct tagatgcacc taccttaccc | 1260 |
| tccactcctc tcattggtca caaactgaca ccatgtcgag accagactgt gaaaacccag | 1320 |
| aaggaaaatt ccatctttag aactccagct atcaaaaggt caatcctcga agctctcct | 1380 |
| cgaactccca caccattcaa acatgccctt gcagctcaag aaattaaata cggtcccctg | 1440 |
| aagatgctac ctcagacccc ctcccatgca gtggaggacc tacaagatgt gattaagcgg | 1500 |
| gaatcggatg aatctggaat tgttgctgag tttcaagaga gtggaccacc gttactgaaa | 1560 |
| aaaatcaagc aggcggtgga gtcgccaact gagaaatcgg gaaacttctt ctgctcaaac | 1620 |
| cactgggcag agaacagcct gagcacccaa ctgttctcgc aggcgtctcc tgtggcagat | 1680 |
| gccccaaata ttcttacaag ctctgttta atgacacctg tatcagaaga tgaagacaat | 1740 |
| gtcctcaaag cctttaccgt acctaagaac aggcccctgg tgggtccctt gcagccatgc | 1800 |
| agtggtgcct gggagccagc atcctgtggg aagacagagg accagatgac ggcctccggt | 1860 |
| ccggctcgga aatacgtgaa cgcgttctca gctcgaactc tggtcatgtg aga | 1913 |